United States Patent
Mori et al.

(10) Patent No.: US 7,259,292 B1
(45) Date of Patent: Aug. 21, 2007

(54) METHODS OF PRODUCING TRANSGENIC GRAMINEAE PLANTS HAVING RESISTANCE TO IRON DEFICIENCY

(75) Inventors: Satoshi Mori, Tokyo (JP); Hiromi Nakanishi, Tokyo (JP); Michiko Takahashi, Tokyo (JP); Naoko Nishizawa, Tokyo (JP)

(73) Assignee: Japan Science and Technology Agency (JP)

( * ) Notice: Subject to any disclaimer, the term of this patent is extended or adjusted under 35 U.S.C. 154(b) by 603 days.

(21) Appl. No.: 10/019,783

(22) PCT Filed: Jul. 4, 2000

(86) PCT No.: PCT/JP00/04425

§ 371 (c)(1),
(2), (4) Date: Apr. 26, 2002

(87) PCT Pub. No.: WO01/01762

PCT Pub. Date: Jan. 11, 2001

(30) Foreign Application Priority Data

Jul. 5, 1999  (JP)  ................. 11/190318

(51) Int. Cl.
*C12N 15/09* (2006.01)
*C12N 15/82* (2006.01)
*A01H 5/00* (2006.01)
*A01H 5/10* (2006.01)

(52) U.S. Cl. ............... 800/278; 800/298; 800/295; 435/468; 435/69.1

(58) Field of Classification Search ........... 800/278, 800/298, 320, 295, 320.1; 435/69.1, 468

See application file for complete search history.

(56) References Cited

U.S. PATENT DOCUMENTS 5,591,616 A * 1/1997 Hiei et al. ............... 435/469

FOREIGN PATENT DOCUMENTS

EP  0 860 499 A2  8/1998

OTHER PUBLICATIONS

Supplementary European Search Report dated Mar. 24, 2003.
A. Wallace et al., "Iron Chlorosis in Horticultural Plants", American Society for Horticultural Science, vol. 75, pp. 819-839 (1960).
Sei-ichi Takagi et al., "Physiological aspect of magineic acid, a possible phytosiderophore of griminaceous plants," 7(1-5) Journal of Plant Nutrition 469-477 (1984).
N. Nishizawa et al., "The particular vesicle appearing in barley root cells and its relation to mugineic acid secretion." 10(9-16) Journal of Plant Nutrition 1013-1020 (1987).
Shinsuke Shojima et al., "Biosynthesis of Phytosiderophores", 93 Plant Physiol. 1497-1503 (Apr. 1990).

(Continued)

*Primary Examiner*—Medina A. Ibrahim
(74) *Attorney, Agent, or Firm*—Rader, Fishman & Grauer PLLC

(57) ABSTRACT

A method for producing transgenic gramineae plants having tolerance to iron deficiency by transforming the plants with a barley gene encoding nicotianamine aminotransferase (NAAT) and transgenic gramineae plants are provided. The present invention also provides transgenic gramineae plants having resistance to iron deficiency which can grow in iron deficiency and calcareous alkaline soils.

9 Claims, 25 Drawing Sheets
(3 of 25 Drawing Sheet(s) Filed in Color)

OTHER PUBLICATIONS

Nami Okumura et al., "An iron deficiency-specific cDNA from barley roots having two homologous cysteine-rich MT domains," 17 Plant Molecular Biology 531-533, Kluwer Academic Publishers (1991).

S. Mori et al., "Why are young rice plants highly susceptible to iron deficiency", Iron nutrition and interactions in plants, 175-188, Kluwer Academic Publishers (1991).

Hiromi Nakanishi et al., "Expression of A Gene Specific for Iron Deficiency (Ids3) in the Roots of *Hordeum Vulgare*," 34(3) Plant Cell Physiol 401-410, JSPP (1993).

Nami Okumura et al., "A dioxygenase gene (Ids2) expressed under iron deficiency conditions in the roots of *Hordeum vulgare*", Plant Molecular Biology 25; 705-719, Kluwer Academic Publishers (1994).

Yukoh Hiei et al., "Efficient transformation of rice (*Oryza sativa L.*) mediated by Agrobactrium and sequence analysis of the boundaries of the T-DNA", 6(2) The Plant Journal 271-283, (1994).

David Eide et al., "A novel iron-regulated metal transporter from plants identified by functional expression in yeast", vol. 93, pp. 5624-5628, Proc. Natl. Acad. Sci., (May 1996).

Nigel J. Robinson, et al., "The froh gene family from *Arabidopsis thaliana*: Putative iron-chelate reductases,"196 Plant and Soil 245-248, Kluwer Academic Publishers (1997).

M. Takahashi et al., " Purification, characterization and DNA sequencing of nicotianamine aminotransferase (NAAT-III) expressed in Fe-deficient barley roots," Plant nutrition, 279-280, Kluwer Academic Publishers (1997).

S. Mori , "Reevaluation of the genes induced by iron deficiency in barley roots", 43 Soil Sci, Plant Nutr., 975-980 (1997).

Kazuya Suzuki et al., "Formate Dehydrogenase, an Enzyme of Anaerobic Metabolism, is induced by Iron Deficiency in Barley Roots," 116 Plant Physiol 725-732 (1998).

Kyoko Higuchi et al., "Cloning of Nicotianamine Synthease Gene, Novel Genes Involved in the Biosynthesis of Phytosiderophore," 119 Plant Physiology 471-479 (Feb. 1999).

Jian Feng Ma et al., "Biosynthesis of Phytosiderophores in several *Triticeae* species with different genomes," vol. 50, No. 334, pp. 723-726, Journal of Experiment Botany, (May 1999).

M. Takahashi et al., "Cloning two genes for nicotianamine aminotransferase, a critical enzyme in iron acquisition (Strategy II) in gramineaceous plants", Plant Physiol., vol. 121[3] 947-956 (1999).

Reiko Itai et al., "Induced activity of adenine phosphoribosyltransferase (APRT) in iron-deficient barley roots: a possible role for phytosiderophore production", vol. 51, No. 348, pp. 1179-1188, Journal of Expeimental Botany, (Jul. 2000).

* cited by examiner

F I G. 4
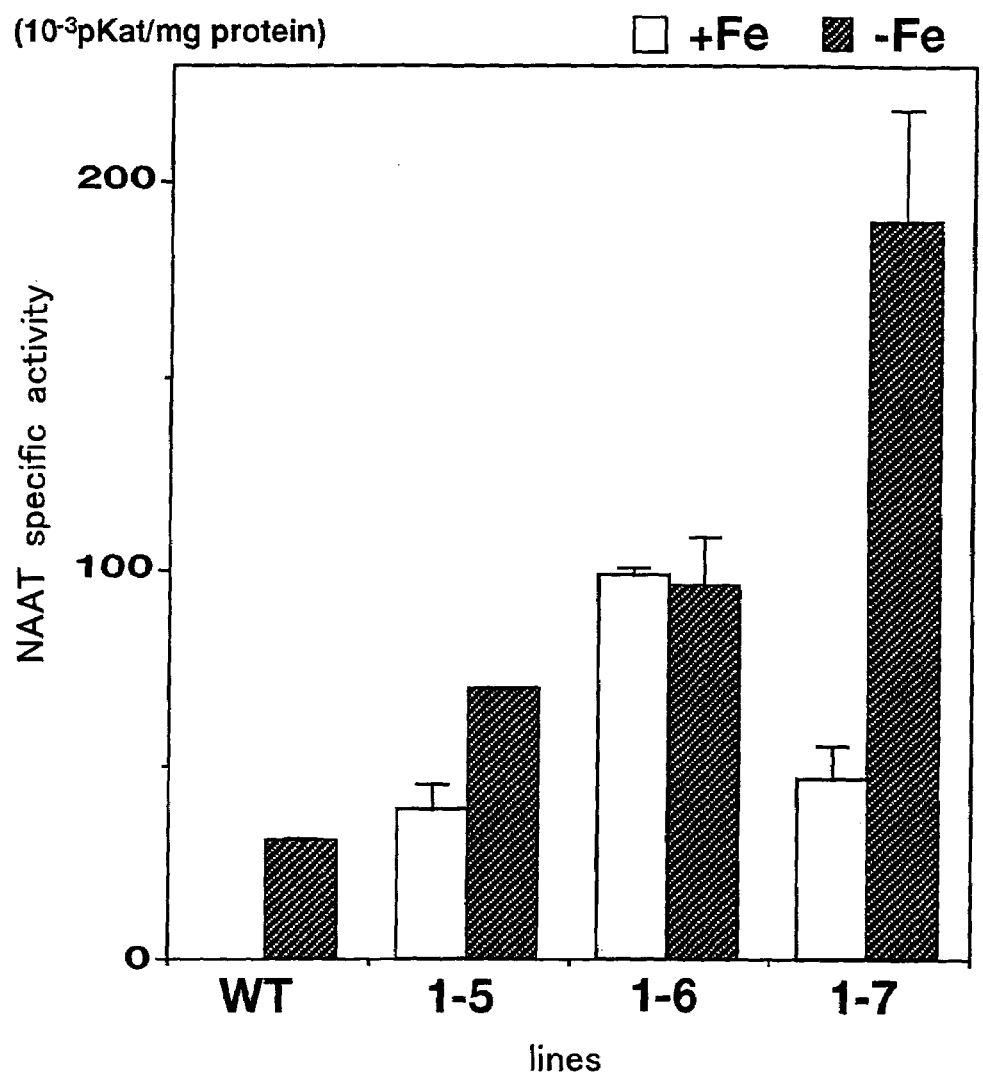

F I G. 7
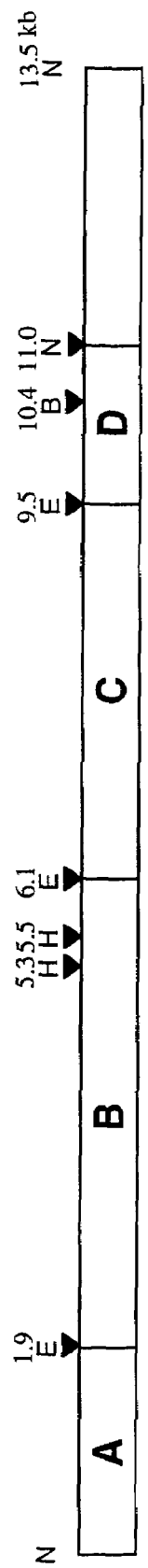
E: EcoRI, H: HindIII, B: BamHI, N: NotI.
The NotI site on both sides is the NotI located at the arm of λFIX II

FIG. 9A

```
CTCGATCCCATTGCAATGGTATGATTAGCTATCAAACGAAAGAAAGAGATGGCATGTGCC
CTGTGTGTCATCCCTCACTGGCTTGGCGAATGGCGATACCGAGTTAGGTAGAGTGTTTTT
TTAGCATGATGTCTGCCGGCACTGCCAAGAAAACTGCGTGCAGCGGACTGCAGGAGAGTT
GAGCGATGCATGCTTTGTGATGAGCGGAGCTGAGTGGGTGTCACTAACTGAACCCAATCA
GCATTGGGTGAGTCGAGTCGAGAAGCATCATGCTTCCTGCGTCCCGATCCGCTTATCTTT
TTCTCCCAAATTATTAAAGAGGGATAGATGATGGTGTGCTGGGTTGGGTAGAGTACGTGC
ATAGAACCAAAGCGAGGCGCCGAAAATATGCCGGGGATAATGGTGGCAGGCCGCAACGGC
CACGCCCGTCAGCTGGCAGCGGCGTGCCAGAGCGTGCCAGAGCGTGCGCGCGTGCGTGCT
TCTTGCTGCCGGCCCCGGTTCGTGTGCGGTCAGAGCAACGGCTATATAGGACCGTCAATC
ACCGCTACTCAATCCGTCCCCAACTCGTTTCCTATTACCGCTACTAGTAGTATTCCTGGT
GTAGTCTAGTAGTACTCCTCCTCCTCCTTCTCCTCCTACCCGTTTCCTCATGGCCACCGT
ACGCCAGAGCGACGGAGTCGCCGCGAACGGCCTTGCCGTGGCCGCAGCCGCGAACGGCAA
GAGCAACGGCCATGGCGTGGCTGCCGCCGTGAACGGCAAGAGCAACGGCCATGGCGTGGA
TGCCGACGCGAACGGCAAGAGCAACGGCCATGGCGTGGCTGCCGACGCGAACGGCAAGAG
CAACGGCCATGCCGAGGCCACTGCAACGGCCACGGCGAGGCCACTGCAACGGCAAGAC
CAACGGCCACCGCGAGAGCAACGGCCATGCTGAGGCCGCCGACGCGAACGGCGAGAGCAA
CGAGCATGCCGAGGACTCCGCGGCGAACGGCGAGAGCAACGGGCATGCGGCGGCGGCGGC
AGAGGAGGAGGAGGCGGTGGAGTGGAATTTCGCGGGTGCCAAGGACGGCGTGCTGGCGGC
GACGGGGGCGAACATGAGCATCCGGGCGATACGGTACAAGATCAGCGCGAGCGTGCAGGA
GAAGGGGCCGCGGCCCGTGCTGCCGCTGGCCCACGGGGACCCGTCCGTGTTCCCGGCCTT
CCGCACGGCCGTCGAGGCCGAGGACGCCGTCGCCGCCGCGCTGCGCACCGGCCAGTTCAA
CTGCTACCCCGCCGGCGTCGGCCTCCCCGCCGCACGAAGGTAACAACAACAACAACACAA
GAACAATTTCCTTTTCGCGTGTCGTGTCGCGCGGCAATCCATGCATGCGCATGTGCCGCT
TTCACGTGTCCGTCCGTCCGTCCACCGTTCCTTCCTCCTCCCTACGCCCATGAGAAATCT
GACCTTCTCCCACCTTATACCAAACAAAACAAAAAAACACAGCGCCGTGGCAGAGCACCT
GTCGCAGGGCGTGCCGTACATGCTATCGGCCGACGACGTCTTCCTCACCGCCGGCGGGAC
CCAGGCGATCGAGGTCATAATCCCGGTGCTGGCCCAGACCGCCGGCGCCAACATTCTGCT
CCCCAGGCCAGGCTACCCAAACTACGAGGCGCGCGCCGCGTTCAACAGGCTGGAGGTCCG
GCATTTCGACCTCATCCCCGACAAGGGGTGGGAGATCGACATCGACTCGCTGGAATCCAT
CGCCGACAAGAACACCACCGCCATGGTCATCATAAACCCCAACAACCCGTGCGGCAGCGT
TTACTCCTACGACCATCTGTCCAAGGTTTCACATCCTTTGCCTTGCTGAATATGGATTCA
GTTCAGTGCACCTGCTGAATTCTTTTTGCCAATCGCATACTGACTGATGTTGCTCAATTA
GGTCGCGGAGGTGGCGAAAAGGCTCGGAATATTGGTGATTGCTGACGAGGTATACGGCAA
GCTGGTTCTGGGCAGCGCCCCGTTCATCCCAATGGGAGTGTTTGGGCACATCACCCCTGT
GCTGTCCATAGGGTCTCTGTCCAAGTCATGGATAGTGCCTGGATGGCGGCTTGGATGGGT
AGCGGTGTACGACCCCAGAAAGATCTTACAGGAAACTAAGGTACTTAAATCTCTATATCA
TTCTTTTCAAATGCTACTAAGGTGATTAATTAGTACTACTGTACAATATATTTGCTAAAT
TTGTACTGACATTTTTGTGGTAGATCTCTACATCAATTACGAATTACCTCAATGTCTCGA
CAGACCCAGCAACCTTCATTCAGGTCAGTCTTTGGTATTTACCTCGTTTCAAGAAATAAA
GTCTTTGGTATTTACTCCTCCTTGTCCTATTTTGCTCCGGTCCCTATGTTGTAGGCAGCC
CACGTGCATGTCAAGTGACCGTTTTTTCACATTAAGTTTGAAAGTCAAAGTCAGACACAT
ACACTTGTAGTTATTTTACCTTTGTTTGCTTTGATCCGATAAAATAAAAAAATACAAAAA
CTGAACCTACTGTTGAATATAACCACTGTTCTTACAAGATATACATGATTGCACTATGGG
CATGCCATATTCTTTTGGGTCAAGTATGCAGTATGTTGGAACCTCTTTTAGAAAATAGAT
ACATTGTACTATGAGTATACCATTTATTAAGAATTTCATATTTTGATATCCTTGATGGT
ATTGTTCTCTTGTGATTCACACGATTTACTTGTGGTTTTTTGTACTATCAAATTGTTCAG
GCAGCTCTTCCTCAGATTCTTGAGAACACAAAGGAAGATTTCTTTAAGGCGATTATTGGT
CTGCTAAAGGAATCATCAGAGATATGCTACAAACAAATAAAGGAAAACAAATACATTACA
TGTCCTCACAAGCCAGAAGGATCAATGTTTGTCATGGTAAGCCTATTTTGTGAAGTAAAA
AAATCTTAGGGAGTGTCAGTAATCATAAACTTATTTATATAGGATTAATCTGGGACCGAA
```

FIG. 9B

```
ATGCATCCAACATAATTACTTCAAATTCAAATTCAAATTACATTCTTCCGTACATATTTT
TGAAGATGCATGTATTTTAAGAATAATGACGAGAGCTAAAGTTATGCTACGACTAATCAT
CTGGATATCCTTTGTCCATCTTTTTGTTATACTGTGGAATGTTAATGGTCAAATCATATT
ACACAAATATCCATGCTAGTTTCTAGAAAGATTGATTATTTTCTGTAACCATGAACTCC
GTATTAACTTCCATGTAAACAGGTGAAACTGAACTTACATCTTTTGGAGGAAATAGACGA
TGACATTGATTTTTGCTGCAAGCTCGCAAAAGAAGAATCAGTAATCTTATGCCCAGGTAG
GAATCCATTGTTGATTTTTGACTGTATATGAAGTTCTTATCAATTTCCGAGATGACTATA
CATATAAATGATTACCATATTATGGTCAGAAATTGTATAACAGTGTTAGAATATTCTGTG
AAGACTTTTTTAACACAATATTCTGTGAAGACTAGATATCATGTACTTCTCCTTGTTTTC
TTGACCTGATGTCCTTCGTCACATGTTGTGCTCCTCACAAAAAAATAGCAAGCACATGTT
TCAAATAATTGTTAATAATATAATTTAGCCTTTAATTTATATGGTTCTATTTTGAGATAT
TTTTGTAGTCCAACTTATATATTTGTGACTATTCTCAAAAACAAAACTTATATATGTGTG
CCTCTCAAATGTAGGGAGTGTTCTTGGAATGGCAAACTGGGTCCGCATTACTTTTGCTTG
TGTTCCATCTTCTCTTCAAGATGGTCTCGGAAGGATCAAATCATTCTGTCAAAGGAACAA
GAAGAGAAATTCGAGCGATGATTGCTAGTTGTATATCTGACTGAAGCTGTAAATCATTCC
CAGTATCCCCATCTATATCTTTCAATAAAATGGAACTTTTAGTTCTCTATGAATAGAAGT
CAACATCTCCTTGAATATGTTCTGGTTGTTGTGGCCTGGACGAAACATAGTGAATGTTAT
GTTAGTGAAGTTACATTGGCGTCGAAGATCTTTGAAGTTTTTTTTTTTTTTGGGGGGGG
GGGGGGGGGGTGCTTTGATATTACTCTTAAGTACACGTTCTCTCAAGTTATGTCAAAGCA
CTTTGTAAACAATTGTAGATTTGGTATCATGATATGGATTAAACTAGTCAGATACTTGGT
AAGCACAAACCCTACCTATGTTAGGCTCACTAAGGTGGCGTTTGGTTCGAGAGAGAGGAA
GGATCAGTTGATGATATCCCCAATCATCGAAGTAAATCATGTGTTGTTGCTACCACTTTT
CTACAATCCTAGTAGCTGCATGCGTTGAGCTACTGATCAACACCACTGCACAACCATATT
CTCTGTGCAAAATCGGCACCCAAAGATTACATCTCACAGCTGAAGCAACCACCAAATTTG
AAGAGAGGAACCCTCACAAAGACCTTTGAGTGCCCCCCACAATGCATGGTTAGGCCGCCG
TCGCAGGCCGGAGTGGTCACCATGCGGACCAACACCAACTCCAACGGGGGAGCACGTCAC
CGATTACTGAAATTCCCCAAACAATTCTTAATTTGTGAACAAAATTTAAAAACAGGAACA
ATTTTTGAATTTGTGAACAAATTTTTTAAACGGGTATTCCTGAACATTTTTCAAAATTGT
GATCAAAATTTTAAAACGACTTCTTTCTCAAATTTGAGCAATATTTAAAATTATAAAAAA
GTTCAACAATTTTGAACTTTTTAAAAATTAGCGAGAACATTTTGAAATTCTAAATATTTT
CGAATTTGGAACATTTTTTCTATTTCTGAACAAAAATTGAAAATACGAACGTAATTTGGA
ATAAATTTTGGAAAATGCGATTTTTTGAAATTTCTGAACATATTTTGAAAAACAAAAAAA
CTTTAAAAGGTAAAATAAAAATAAAATAAAAATAGAAACATAAAAATAAGCAAAAAAATA
AAAGAAATCCGAGAAAAGCCAACTGGGAATAGCACATGGAAAAACCCAGCCGTCCGCCGC
ACTGTGTAAAGCTATAAGTGAGCCGGCCCAAGCCTCGTCGTCTCATCATACCCTGTGCGA
AACCCCGACAATTCGTTGCACTATGCGGCGAATAGGCTTTTCCAGGAGCTCCTGTCTTCC
GGTTATGGGTCATTTGCACACCCCTCCTCCACTTGGGCCAGGCTATTATACTTTTTTTCC
TTCTTTCGACCTCACGTTACTACGCCAGTTTAGTTTTTGGAAGCGACCAACCGGTTTTGT
GAAGGTTCTAGAAACTCAACCATTTTTGGGAAGCTTCTAGAAGCCTATGAATGTTTCTTT
TGGACATGTATTATTTGTGTTTTTTCTTTTTCAAATTGCACAATCTTTTTTCAAATTCAT
GATTTTTGTGAAACTTGTGATTTTTTGAATCCGTGATTTTTTTCCTAAATCCGTGTTTT
GAAAAAAACTGTGGACTTTTCCGAAATTAATGAACATTTGTTTGCAAGATCGATGATCCT
TTTCAAATGAGCGATTTTTTTCTAAAATATCCACATATTTTTCATATTCATAAGCTTTCC
TTTTAATCGTGAACTATCTTAGCATTTGGTGAACTTTTATTAATTTCTTTATAAAATGA
TTTTTTTTCAAAAGCCAACGGTTAACGGTTGACCGCTGAACCACAACCACAAACCGGGGA
AACCATTGACTCGCTGAACAGGGCAGGGCTTTCATATGATTGGGTGGTCTAATACCAGCG
CCCCTGACTACTAAACGAAGGAATTGCAAATTTTACCAACCACTACTATGGTAAAAAATG
AATATCACGATAAAAAGGGGAAAAAAACTATACCCTGAAAATCCCTCTGTTTCTAAAT
ATTTGTTGTTGGGGAGAACTAATCTGAAAGAACTAATCTAGTTCTCCGCAATAACAAATA
TTATGATTCGGGGGGAGTATAACTATTACACGATCAACCAAAGAATGTCCTCCAAGAAAA
ACCCAAAGAAAGTGCTAGAGTTTTGTTTTCAAGGACCGAAAGATAGAGATAGCATTCTGA
ATTAGGTCCATCTTTTTCCCAAGGATTGAAAGAAAGAGATAGAATTCTGAATTAGGTGCG
```

FIG. 9C

```
GAGATATCATTTCTGGATTAGGTACAATTGTTTTGCCGGCACAGCCAAACCCCGCAGTGG
AGCCGGAATTGGAATTGAGTGGGTGGAGTCGAGAAGCATGGTTCATGCGTTCTCAAAGAG
TGTAGCCAGTAGTGTGTGCTCCTTGGTGCTGGAGCTGCATATACAAGTACATAAAACAAA
GACGATCAGCTGGCAGCGTGCCTGCATGCGTGCTTCTTGCTGCCGCCCCGGAAGCCCCGG
TTGATGTGCGCAGGCGAGTGGCGACGGGACCGACGGCTATAAAGCACGGCCAAGCACCGC
CGCCGTTCTCAATCCATCCATCCCTTAGCTGATTTGATTGACTAGCTAGTTCATTCCCTG
CCACACTGCTAGTACTCCTCCTCGTTTCCTCGTGGCAATGGTACACCAGAGCAACGGCCA
CGGCGAGGCCGCCGCCGCCGCCGCCAACGGCAAGAGCAACGGGCACGCCGCCGCCGCGAA
CGGCAAGAGCAACGGGCACGCGGCGGCGGCGGCGGTGGAGTGGAATTTCGCCCGGGGCAA
GGACGGCATCCTGGCGACGACGGGGCGAAGAACAGCATCCGGGCGATACGGTACAAGAT
CAGCGCGAGCGTGGAGGAGAGCGGGCCGCGGCCCGTGCTGCCGCTGGCCCACGGTGACCC
GTCCGTGTTCCCGGCCTTCCGCACGGCCGTCGAGGCCGAGGACGCCGTCGCCGCCGCGCT
GCGCACCGGCCAGTTCAACTGCTACGCCGCCGGCGTCGGCCTCCCCGCCGCACGAAGGTA
ACATTTACAGCTTCACCGTAATGTATGCGTGAGCATGCATGCGCCGGTTTACTTACGTGC
CCGCCGCTGTTCTTCCCCGGTGCGTTCAAAATTTTAACCTTCTATAAGTACCTTATAAAA
ACAAACAGCGCCGTAGCAGAGCACTTGTCACAGGGCGTGCCCTACAAGCTATCGGCCGAC
GACGTCTTCCTCACCGCCGGCGGAACTCAGGCGATCGAAGTCATAATCCCGGTGCTGGCC
CAGACTGCCGGCGCCAACATACTGCTTCCCCGGCCAGGCTATCCAAATTACGAGGCGCGA
GCGGCATTCAACAAGCTGGAGGTCCGGCACTTCGACCTCATCCCCGACAAGGGGTGGGAG
ATCGACATCGACTCGCTGGAATCCATCGCCGACAAGAACACCACCGCGATGGTCATCATA
AACCCAAACAATCCGTGCGGCAGCGTTTACTCCTACGACCATCTGGCCAAGGTTTTGCAT
CCATGCATCCTCTGCCTCGTTGATCGACCGGTCTGTTTGAACATAGTATATGGATTGCGT
TTGCTAATCGTGTGCTGATGATGCTGTTTGGTTATCAGGTCGCGGAGGTGGCAAGGAAGC
TCGGAATATTGGTGATCGCTGACGAGGTTTACGGCAAACTGGTTCTGGGCAGCGCCCGT
TTATCCCGATGGGCGTCTTTGGGCACATTGCCCCGGTCTTGTCCATTGGATCTCTGTCCA
AGTCGTGGATAGTGCCTGGATGGCGACTTGGATGGGTGGCGGTGTACGACCCCACAAAGA
TTTTAGAGAAAACTAAGGTAGCTTTAGCTCCCTATCATTCTTCTCATATGCTACTGTGGG
GATTAGTATTTTTGCTAAATTTGTACTGCCTTTGTTTATTCAGATCTCTACGTCTATTAC
GAATTACCTTAATGTCTCAACGGACCCAGCAACCTTCGTTCAGGTTAGTCTTTGGTTCTT
GCCCTATTTTGCTCATGTCCCTGTGTTGCATGTCAAATGACCGGCTTCAAGTTAGTATAT
AGAGTTTTTGTTAAGTGTGAATGTCGAAGTCCAACATGATGGAAGAAAGATACATCTATT
TTTAGTCATTCCCCTTTGTTTGTTTGATTCCATAAAATAAATAAACACAAAGCCAGAACC
AACTATTGAATAGAACTATTTTTCTTAGAAAATATACATTGTATTTGAGCATGCCATAT
TCTTTTCGATCAAGTATGCAATATATTAAAACTTGCATTGTACTACGAGTATACCATGTT
GTTAAGAATTTCTTTACCTACAACACCTTGTCTCGCATCTTCATATTTTGATATCCTTGA
CATTATTGTTCTCTTATGATTCACACAACTTAATTATGGATTTTGTGCTATCAAATTGT
TTAGGAAGCTCTTCCTAAAATTCTTGAGAACACAAAAGCAGATTTCTTTAAGAGGATTAT
TGGTCTACTAAAGGAATCATCAGAGATATGTTATAGGGAAATAAAGGAAAACAAATATAT
TACGTGTCCTCACAAGCCAGAAGGATCGATGTTTGTAATGGTAAGCTAAGCATAGACTTA
CTTTTTAAGGTTAATCTGGGATCTCAGTGCATCCAACAAACAATCAAATCAAAATATAAT
TATGTTTTGCTATGGATCTTTTTGAAGATGCATGCATTTGAAGAATAATGAAGAGAGTTG
AAATTATTTTAGGACTAATCTTCCTGATATCATTTGTCCATTTTTTTGTTATTACTGTAA
ATTGGTAACACTCAAATCATATTACAAAAAGTTTCCTCCCATTTTTAGTAAGATTGACTT
CCTTTCTATAACCATGTATTAACTTCCATGTAAACAGGTCAAACTAAACTTACATCTTTT
GGAGGAGATCCATGACGACATAAATTTTTGCTGCAAGCTCGCAAAGGAAGAATCTGTAAT
TTTATGTCCAGGTAGGAATGTATATGGCCATTTTAAAGGAAAACTATATGGAATAATAAT
ATCTTCTTGTTATACTAAACAATACTTCCTCCATCCTAAAATAAATGTCTTACACTTAGC
ACAATTTTATACTAGATCTAGTACAAAGTTGAAACAGTTATTTTGGGACAGAGGGAGTAG
TATATATTGTGTGAGAACATAAGGTTATGTTTGACTGATATATGCTTCTTAAATGTGAAA
CATGTTCTCTTATGTTTTTTGATTGTATACGAAGTTCTTATCAGTTTCCGAGATGACTAC
ACATAAATGATTACCATATCATTGTCAGAAAATGTATTACCACATTAGAATATTCTTTCT
TTTTATGCAAAGACTAGCATGGCATGTACTTTTCCTTGTACCTATGTGTCTTTTTTTTC
```

FIG. 9D

```
TCGTTACATGTTTGTGCTTCTCACAAAAATAATAATACCAAGCACATGTTCCAAATGATT
ATTAATAATTTTGAGGTGTTTTTCAACCAACTTATATACTTTCATAGTTCTAAAAAAACC
GTATATATGGTTAACTCTAACAAAAACTTATATATGTTTTCTCTCTAATACAGGGAGTGT
TCTTGGAATGGAAAATTGGGTCCGTATTACTTTTGCCTGCGTTCCATCTTCTCTTCAAGA
TGGACTCGAAAGGGTCAAATCATTCTGTCAAAGGAACAAGAAGAAGAATTCTATAAATGG
TTGTTAGTTGTACACACCCCTAGTTGTACATCTGACTGAAGCTGTAAATCATTTCTAGTT
ATCCCCATTTATATATTTCAATAAAACATATTGTAATGGTTCTGTTGTAGCTGTCCAAGT
CATGTACTCTACTTTTTGATGTATTTGGCCTCATTGCCTTGCATCAGTTTCAATAAAAAT
GGTTGTGTACACAATGATGATGTAGAGGCGAGGTGTTTTGACCACCTTTTCAACAAAAAT
CTATATCTTTCAACAAATGAAACCTTGAGTTCCCTTTGAGTAGAAGTCAACATACTCCTT
GAATATGCTATGGTTTCCATGGTCTGGATGAAACATGATGAATAGAAGTGAAGTTATATC
CATGTCAAAGTTTTTTAATGTTTAATTTCATTATGAGAACTTTGATATTACTTCTAGCAC
ACATTCTCTGAAGTAATTGTCAGTTTGGTACTTGAAGGGACCTATATTTTTCCTATTGGG
GGGGGGGGGTGAATAGGCGGTTTATAACCAATTGTATATTTGAGAATATCTTAATGTGGA
ATTAAACTAGGTGAATATTTTTTCCAATAAAGGGTGCTTTTATTGACTCACAATGTACCA
TCAAGGGATACAATCATAATGAGTACACAATCGACATCTACATAATCAGGTTGCATACGG
CCAACACACACACACGCACACACACATTCACACACACAAATCATGCTGACGAAGAGCGAA
GTCATACAAGATCAAAACTATGCCTAGGCGGAGGAAGAATAGAAAAACATGAAGAAATGA
AAAACCGTGACTGACAACATACTGACCATCGACGACAAACATCTGTAGACAACACAAAAA
CTGCGAGAAAAGTTCTATAAAACTGGCGCCTTCGAGAAGGAAACGACGTGCAAGAGTTGC
CATCATCGGATCCAACCACTAAGGTCATATCCTGGGTTTTCATCCTGAAGATCAAATCCG
AGCAAACTCCGAGTAATGTCTTTATTAGGGTAACGATTCAAAAAATGCCACAATCATGAG
TTATGACCAATTAGACCAGACCTAGGATTTTTATCCAAAGCTCGAGACGGGTACTCTAGA
AGTACCATCCAATTGAAGTCATCCCACTTGCCTCAATACAAATAGTTGCATAGATGCACG
GTCCATATGGCGAGTAATGGACATGAGCGCGCATGTGTAGGTTAACGTGACGTGACAAGA
GCCTGTCGCCACCACTCGACGAAGTGTTTGATGGGGAGGAAGAAGTATGGCTCCACCAAC
ATCCCAAGTTTGAAACATTCTAGAGCCCCTTACCATACTCACAAAGCGACAATTGATGAC
TATCTGTATCAGACGACAAATCCATGTCCGTCACTCGCTCTATCTTGGTCATTGACATAC
TACCTGGCAAAGGCGGATTCAAGCCCCAGACAGCCTGGGCGGCCGC
```

FIG. 10A

```
ctcgatcccattgcaatggtatgattagctatcaaacgaaagaaagagatggcatgtgcc
ctgtgtgtcatccctcactggcttggcgaatggcgataccgagttaggtagagtgttttt
ttagcatgatgtctgccggcactgccaagaaaactgcgtgcagcggactgcaggagagtt
gagcgatgcatgctttgtgatgagcggagctgagtgggtgtcactaactgaacccaatca
gcattgggtgagtcgagtcgagaagcatcatgcttcctgcgtcccgatccgcttatcttt
ttctcccaaattattaaagagggatagatgatggtgtgctgggttgggtagagtacgtgc
atagaaccaaagcgaggcgccgaaaatatgccggggataatggtggcaggccgcaacggc
cacgcccgtcagctggcagcggcgtgccagagcgtgccagagcgtgcgcgcgtgcgtgct
tcttgctgccggccccggttcgtgtgcggtcagagcaacggctatataggaccgtcaatc
accgctactcaatccgtccccaactcgtttcctattacCGCTACTAGTAGTATTCCTGGT 600
GTAGTCTAGTAGTACTCCTCCTCCTCCTTCTCCTCCTACCCGTTTCCTCATGGCCACCGT
                                                       M  A  T  NAAT-B ACGCCAGAGCGACGGAGTCGCCGCGAACGGCCTTGCCGTGGCCGCAGCCGCGAACGGCAA
 R  Q  S  D  G  V  A  A  N  G  L  A  V  A  A  A  A  N  G  K GAGCAACGGCCATGGCGTGGCTGCCGCCGTGAACGGCAAGAGCAACGGCCATGGCGTGGA
 S  N  G  H  G  V  A  A  A  V  N  G  K  S  N  G  H  G  V  D TGCCGACGCGAACGGCAAGAGCAACGGCCATGGCGTGGCTGCCGACGCGAACGGCAAGAG
 A  D  A  N  G  K  S  N  G  H  G  V  A  A  D  A  N  G  K  S CAACGGCCATGCCGAGGCCACTGCGAACGGCCACGGCGAGGCCACTGCGAACGGCAAGAC
 N  G  H  A  E  A  T  A  N  G  H  G  E  A  T  A  N  G  K  T CAACGGCCACCGCGAGAGCAACGGCCATGCTGAGGCCGCCGACGCGAACGGCGAGAGCAA
 N  G  H  R  E  S  N  G  H  A  E  A  A  D  A  N  G  E  S  N CGAGCATGCCGAGGACTCCGCGGCGAACGGCGAGAGCAACGGGCATGCGGCGGCGGCGGC
 E  H  A  E  D  S  A  A  N  G  E  S  N  G  H  A  A  A  A  A AGAGGAGGAGGAGGCGGTGGAGTGGAATTTCGCGGGTGCCAAGGACGGCGTGCTGGCGGC
 E  E  E  E  A  V  E  W  N  F  A  G  A  K  D  G  V  L  A  A GACGGGGGCGAACATGAGCATCCGGGCGATACGGTACAAGATCAGCGCGAGCGTGCAGGA
 T  G  A  N  M  S  I  R  A  I  R  Y  K  I  S  A  S  V  Q  E GAAGGGGCCGCGGCCCGTGCTGCCGCTGGCCCACGGGGACCCGTCCGTGTTCCCGGCCTT 1200
 K  G  P  R  P  V  L  P  L  A  H  G  D  P  S  V  F  P  A  F CCGCACGGCCGTCGAGGCCGAGGACGCCGTCGCCGCCGCGCTGCGCACCGGCCAGTTCAA
 R  T  A  V  E  A  E  D  A  V  A  A  A  L  R  T  G  Q  F  N CTGCTACCCCGCCGGCGTCGGCCTCCCCGCCGCACGAAGgtaacaacaacaacaacacaa
 C  Y  P  A  G  V  G  L  P  A  A  R  S gaacaatttccttttcgcgtgtcgtgtcgcgcggcaatccatgcatgcgcatgtgccgct
ttcacgtgtccgtccgtccgtccaccgttccttcctcctccctacgcccatgagaaatct
```

FIG. 10B

```
gaccttctcccaccttataccaaacaaaacaaaaaaacacagCGCCGTGGCAGAGCACCT
                                            A  V  A  E  H  L GTCGCAGGGCGTGCCGTACATGCTATCGGCCGACGACGTCTTCCTCACCGCCGGCGGGAC
 S  Q  G  V  P  Y  M  L  S  A  D  D  V  F  L  T  A  G  G  T CCAGGCGATCGAGGTCATAATCCCGGTGCTGGCCCAGACCGCCGGCGCCAACATTCTGCT
  Q  A  I  E  V  I  I  P  V  L  A  Q  T  A  G  A  N  I  L  L CCCCAGGCCAGGCTACCCAAACTACGAGGCGCGCGCCGCGTTCAACAGGCTGGAGGTCCG
  P  R  P  G  Y  P  N  Y  E  A  R  A  A  F  N  R  L  E  V  R GCATTTCGACCTCATCCCCGACAAGGGGTGGGAGATCGACATCGACTCGCTGGAATCCAT
  H  F  D  L  I  P  D  K  G  W  E  I  D  I  D  S  L  E  S  I CGCCGACAAGAACACCACCGCCATGGTCATCATAAACCCCAACAACCCGTGCGGCAGCGT 1800
  A  D  K  N  T  T  A  M  V  I  I  N  P  N  N  P  C  G  S  V TTACTCCTACGACCATCTGTCCAAGgtttcacatcctttgccttgctgaatatggattca
 Y  S  Y  D  H  L  S  K gttcagtgcacctgctgaattcttttgccaatcgcatactgactgatgttgctcaatta
gGTCGCGGAGGTGGCGAAAAGGCTCGGAATATTGGTGATTGCTGACGAGGTATACGGCAA
  V  A  E  V  A  K  R  L  G  I  L  V  I  A  D  E  V  Y  G  K GCTGGTTCTGGGCAGCGCCCCGTTCATCCCAATGGGAGTGTTTGGGCACATCACCCCTGT
  L  V  L  G  S  A  P  F  I  P  M  G  V  F  G  H  I  T  P  V GCTGTCCATAGGGTCTCTGTCCAAGTCATGGATAGTGCCTGGATGGCGGCTTGGATGGGT
  L  S  I  G  S  L  S  K  S  W  I  V  P  G  W  R  L  G  W  V AGCGGTGTACGACCCCAGAAAGATCTTACAGGAAACTAAGgtacttaaatctctatatca
  A  V  Y  D  P  R  K  I  L  Q  E  T  K ttcttttcaaatgctactaaggtgattaattagtactactgtacaatatatttgctaaat
ttgtactgacatttttgtggtagATCTCTACATCAATTACGAATTACCTCAATGTCTCGA
                        I  S  T  S  I  T  N  Y  L  N  V  S CAGACCCAGCAACCTTCATTCAGgtcagtctttggtatttacctcgtttcaagaaataaa
T  D  P  A  T  F  I  Q gtctttggtatttactcctccttgtcctattttgctccggtccctatgttgtaggcagcc 2400
cacgtgcatgtcaagtgaccgttttttcacattaagtttgaaagtcaaagtcagacacat
acacttgtagttattttacctttgtttgctttgatccgataaaataaaaaaatacaaaaa
ctgaacctactgttgaatataaccactgttcttacaagatatacatgattgcactatggg
catgccatattcttttgggtcaagtatgcagtatgttggaacctcttttagaaaatagat
acattgtactatgagtataccattttattaagaatttcatattttgatatccttgatggt
attgttctcttgtgattcacacgatttacttgtggttttttgtactatcaaattgttcag
GCAGCTCTTCCTCAGATTCTTGAGAACACAAAGGAAGATTTCTTTAAGGCGATTATTGGT
 A  A  L  P  Q  I  L  E  N  T  K  E  D  F  F  K  A  I  I  G
```

FIG. 10C

```
CTGCTAAAGGAATCATCAGAGATATGCTACAAACAAATAAGGAAAACAAATACATTACA
 L  L  K  E  S  S  E  I  C  Y  K  Q  I  K  E  N  K  Y  I  T

TGTCCTCACAAGCCAGAAGGATCAATGTTTGTCATGgtaagcctatttgtgaagtaaaa
 C  P  H  K  P  E  G  S  M  F  V  M aaatcttagggagtgtcagtaatcataaacttatttatataggattaatctgggaccgaa    3000
atgcatccaacataattacttcaaattcaaattcaaattacattcttccgtacatatttt
tgaagatgcatgtatttaagaataatgacgagagctaaagttatgctacgactaatcat
ctggatatcctttgtccatcttttgttatactgtggaatgttaatggtcaaatcatatt
acacaaatatccatgctagtttctagaaagattgattatttttctgtaaccatgaactcc
gtattaacttccatgtaaacagGTGAAACTGAACTTACATCTTTTGGAGGAAATAGACGA
                       V  K  L  N  L  H  L  L  E  E  I  D  D TGACATTGATTTTTGCTGCAAGCTCGCAAAAGAAGAATCAGTAATCTTATGCCCAGgtag
 D  I  D  F  C  C  K  L  A  K  E  E  S  V  I  L  C  P gaatccattgttgattttgactgtatatgaagttcttatcaatttccgagatgactata
catataaatgattaccatattatggtcagaaattgtataacagtgttagaatattctgtg
aagacttttttaacacaatattctgtgaagactagatatcatgtacttctccttgttttc
ttgacctgatgtccttcgtcacatgttgtgctcctcacaaaaaatagcaagcacatgtt    3600
tcaaataattgttaataatataatttagccttatttatatggttctattttgagatat
ttttgtagtccaacttatatatttgtgactattctcaaaaacaaaacttatatgtgtg
cctctcaaatgtagGGAGTGTTCTTGGAATGGCAAACTGGGTCCGCATTACTTTTGCTTG
               G  S  V  L  G  M  A  N  W  V  R  I  T  F  A  C TGTTCCATCTTCTCTTCAAGATGGTCTCGGAAGGATCAAATCATTCTGTCAAAGGAACAA
 V  P  S  S  L  Q  D  G  L  G  R  I  K  S  F  C  Q  R  N  K GAAGAGAAATTCGAGCGATGATTGCTAGTTGTATATCTGACTGAAGCTGTAAATCATTCC
 K  R  N  S  S  D  D  C  *
CAGTATCCCCATCTATATCTTTCAATAAAATGGAACTTTTAGTTCTCTATGAATAGAAGT

CAACATCTCCTTGAATATGTTCTGGTTGTTGTGGCCTGGACGAAACATAGTGAATGTTAT

GTTAGTGAAGTTAcattggcgtcgaagatctttgaagttttttttttttttggggggggg ggggggggggtgctttgatattactcttaagtacacgttctctcaagttatgtcaaagca
ctttgtaaacaattgtagatttggtatcatgatatggattaaactagtcagatacttggt    4200
aagcacaaaccctacctatgttaggctcactaaggtggcgtttggttcgagagagaggaa
ggatcagttgatgatatccccaatcatcgaagtaaatcatgtgttgttgctaccactttt
ctacaatcctagtagctgcatgcgttgagctactgatcaacaccactgcacaaccatatt
ctctgtgcaaaatcggcacccaaagattacatctcacagctgaagcaaccaccaaatttg
aagagaggaaccctcacaaagacctttgagtgcccccacaatgcatggttaggccgccg
tcgcaggccggagtggtcaccatgcggaccaacaccaactccaacgggggagcacgtcac
cgattactgaaattccccaaacaattcttaatttgtgaacaâaatttaaaaacaggaaca
attttttgaatttgtgaacaatttttaaacgggtattcctgaacattttcaaaattgt
gatcaaaattttaaaacgacttctttctcaaatttgagcaatatttaaaattataaaaa
gttcaacaattttgaacttttaaaaattagcgagaacattttgaaattctaaatatttt    4800
cgaatttggaacattttttctatttctgaacaaaaattgaaaatacgaacgtaatttgga
ataaattttggaaaatgcgattttttgaaatttctgaacatatttgaaaaacaaaaaaa
ctttaaaaggtaaaataaaaataaaataaaaatagaaacataaaaaataagcaaaaaata
```

FIG. 10D

```
aagaaatccgagaaaagccaactgggaatagcacatggaaaaacccagccgtccgccgc
actgtgtaaagctataagtgagccggcccaagcctcgtcgtctcatcatacccttgtgcga
aaccccgacaattcgttgcactatgcggcgaataggcttttccaggagctcctgtcttcc
ggttatgggtcatttgcacacccctcctccacttgggccaggctattatactttttttcc
ttctttcgacctcacgttactacgccagtttagttttttggaagcgaccaaccggttttgt
gaaggttctagaaactcaaccattttttgggaagcttctagaagcctatgaatgtttcttt
tggacatgtattatttgtgttttttcttttcaaattgcacaatcttttttcaaattcat       5400
gattttttgtgaaacttgtgatttttttgaatccgtgatttttttcctaaatccgtgttttt
gaaaaaactgtggacttttccgaaattaatgaacatttgtttgcaagatcgatgatcct
tttcaaatgagcgattttttctaaaatatccacatattttcatattcataagctttcc
ttttaatcgtgaactatcttagcatttggtgaacttttattaattttctttataaaatga
tttttttttcaaaagccaacggttaacggttgaccgctgaaccacaaccacaaaccggggga
aaccattgactcgctgaacagggcagggctttcatatgattgggtggtctaataccagcg
cccctgactactaaacgaaggaattgcaaattttaccaaccactactatggtaaaaatg
aatatcacgataaaaaggggaaaaaaaactatatccctgaaaatccctctgtttctaaat
atttgttgttggggagaactaatctgaaagaactaatctagttctccgcaataacaaata
ttatgattcgggggggagtataactattacacgatcaaccaaagaatgtcctccaagaaaa       6000
acccaaagaaagtgctagagttttgttttcaaggaccgaaagatagagatagcattctga
attaggtccatcttttttcccaaggattgaaagaaagagatagaattctgaattaggtgcg
gagatatcatttctggattaggtacaattgttttgccggcacagccaaacccgcagtgg
agccggaattggaattgagtgggtggagtcgagaagcatggttcatgcgttctcaaagag
tgtagccagtagtgtgtgctccttggtgctggagctgcatatacaagtacataaaacaaa
gacgatcagctggcagcgtgcctgcatgcgtgcttcttgctgccgccccggaagccccgg
ttgatgtgcgcaggcgagtggcgacgggaccgacggctataaagcacggccaagcaccgc
cgccgttctcaatccatccatcccttagctgatttgATTGACTAGCTAGTTCATTCCCTG
```

```
CCACACTGCTAGTACTCCTCCTCGTTTCCTCGTGGCAATGGTACACCAGAGCAACGGCCA
                                     M  V  H  Q  S  N  G  H   NAAT-A

CGGCGAGGCCGCCGCCGCCGCCGCCAACGGCAAGAGCAACGGGCACGCCGCCGCCGCGAA  6600
  G  E  A  A  A  A  A  A  N  G  K  S  N  G  H  A  A  A  A  N

CGGCAAGAGCAACGGGCACGCGGCGGCGGCGGCGGTGGAGTGGAATTTCGCCCGGGGCAA
  G  K  S  N  G  H  A  A  A  A  A  V  E  W  N  F  A  R  G  K

GGACGGCATCCTGGCGACGACGGGGGCGAAGAACAGCATCCGGGCGATACGGTACAAGAT
  D  G  I  L  A  T  T  G  A  K  N  S  I  R  A  I  R  Y  K  I

CAGCGCGAGCGTGGAGGAGAGCGGGCCGCGGCCCGTGCTGCCGCTGGCCCACGGTGACCC
  S  A  S  V  E  E  S  G  P  R  P  V  L  P  L  A  H  G  D  P

GTCCGTGTTCCCGGCCTTCCGCACGGCCGTCGAGGCCGAGGACGCCGTCGCCGCCGCGCT
  S  V  F  P  A  F  R  T  A  V  E  A  E  D  A  V  A  A  A  L

GCGCACCGGCCAGTTCAACTGCTACGCCGCCGGNNTCGGCCTCCCCGCCGCACGAAGgta
  R  T  G  Q  F  N  C  Y  A  A  G  V  G  L  P  A  A  R  S acatttacagcttcaccgtaatgtatgcgtgagcatgcatgcgccggtttacttacgtgc
ccgccgctgttcttccccggtgcgttcaaaattttaaccttctataagtaccttataaaa
acaaacagCGCCGTAGCAGAGCACTTGTCACAGGGCGTGCCCTACAAGCTATCGGCCGAC
         A  V  A  E  H  L  S  Q  G  V  P  Y  K  L  S  A  D
```

FIG. 10E

```
GACGTCTTCCTCACCGCCGGCGGAACTCAGGCGATCGAAGTCATAATCCCGGTGCTGGCC
 D  V  F  L  T  A  G  G  T  Q  A  I  E  V  I  I  P  V  L  A

CAGACTGCCGGCGCCAACATACTGCTTCCCCGGCCAGGCTATCCAAATTACGAGGCGCGA  7200
 Q  T  A  G  A  N  I  L  L  P  R  P  G  Y  P  N  Y  E  A  R

GCGGCATTCAACAAGCTGGAGGTCCGGCACTTCGACCTCATCCCCGACAAGGGGTGGGAG
 A  A  F  N  K  L  E  V  R  H  F  D  L  I  P  D  K  G  W  E

ATCGACATCGACTCGCTGGAATCCATCGCCGACAAGAACACCACCGCGATGGTCATCATA
 I  D  I  D  S  L  E  S  I  A  D  K  N  T  T  A  M  V  I  I

AACCCAAACAATCCGTGCGGCAGCGTTTACTCCTACGACCATCTGGCCAAGgttttgcat
 N  P  N  N  P  C  G  S  V  Y  S  Y  D  H  L  A  K ccatgcatcctctgcctcgttgatcgaccggtctgtttgaacatagtatatggattgcgt
ttgctaatcgtgtgctgatgatgctgtttggttatcagGTCGCGGAGGTGGCAAGGAAGC
                                        V  A  E  V  A  R  K TCGGAATATTGGTGATCGCTGACGAGGTTTACGGCAAACTGGTTCTGGGCAGCGCCCCGT
 L  G  I  L  V  I  A  D  E  V  Y  G  K  L  V  L  G  S  A  P TTATCCCGATGGGCGTCTTTGGGCACATTGCCCCGGTCTTGTCCATTGGATCTCTGTCCA
 F  I  P  M  G  V  F  G  H  I  A  P  V  L  S  I  G  S  L  S AGTCGTGGATAGTGCCTGGATGGCGACTTGGATGGGTGGCGGTGTACGACCCCACAAAGA
 K  S  W  I  V  P  G  W  R  L  G  W  V  A  V  Y  D  P  T  K TTTTAGAGAAAACTAAGgtagctttagctccctatcattcttctcatatgctactgtggg
 I  L  E  K  T  K gattagtattttgctaaatttgtactgcctttgtttattcagATCTCTACGTCTATTAC   7800
                                            I  S  T  S  I  T GAATTACCTTAATGTCTCAACGGACCCAGCAACCTTCGTTCAGgttagtctttggttctt
  N  Y  L  N  V  S  T  D  P  A  T  F  V  Q
gccctatttgctcatgtccctgtgttgcatgtcaaatgaccggcttcaagttagtatat
agagtttttgttaagtgtgaatgtcgaagtccaacatgatggaagaaagatacatctatt
tttagtcattcccctttgtttgtttgattccataaaataaataaacacaaagccagaacc
aactattgaatagaactattttcttagaaaatatacattgtattttgagcatgccatat
tcttttcgatcaagtatgcaatatattaaaacttgcattgtactacgagtataccatgtt
gttaagaatttctttacctacaacaccttgtctcgcatcttcatattttgatatccttga
cattattgttctcttatgattcacacaacttaattatggattttgtgctatcaaattgt
ttagGAAGCTCTTCCTAAAATTCTTGAGAACACAAAAGCAGATTTCTTTAAGAGGATTAT
     E  A  L  P  K  I  L  E  N  T  K  A  D  F  F  K  R  I  I TGGTCTACTAAAGGAATCATCAGAGATATGTTATAGGGAAATAAAGGAAAACAAATATAT  8400
 G  L  L  K  E  S  S  E  I  C  Y  R  E  I  K  E  N  K  Y  I TACGTGTCCTCACAAGCCAGAAGGATCGATGTTTGTAATGgtaagctaagcatagactta
 T  C  P  H  K  P  E  G  S  M  F  V  M
```

FIG. 10F cttttttaaggttaatctgggatctcagtgcatccaacaaacaatcaaatcaaaatataat
tatgttttgctatggatctttttgaagatgcatgcatttgaagaataatgaagagagttg
aaattattttaggactaatcttcctgatatcatttgtccattttttgttattactgtaa
attggtaacactcaaatcatattacaaaaagtttcctcccattttagtaagattgactt
cctttctataaccatgtattaacttccatgtaaacagGTCAAACTAAACTTACATCTTTT
                                                V  K  L  N  L  H  L  L GGAGGAGATCCATGACGACATAAATTTTTGCTGCAAGCTCGCAAAGGAAGAATCTGTAAT
 E  E  I  H  D  D  I  N  F  C  C  K  L  A  K  E  E  S  V  I TTTATGTCCAGgtaggaatgtatatggccatttttaaaggaaaactatatggaataataat
  L  C  P atcttcttgttatactaaacaatacttcctccatcctaaaataaatgtcttacacttagc
acaattttatactagatctagtacaaagttgaaacagttattttgggacagagggagtag  9000
tatatattgtgtgagaacataaggttatgtttgactgatatatgcttcttaaatgtgaaa
catgttctcttatgttttttgattgtatacgaagttcttatcagtttccgagatgactac
acataaatgattaccatatcattgtcagaaaatgtattaccacattagaatattctttct
ttttatgcaaagactagcatggcatgtacttttccttgtacctatgtgtcttttttttc
tcgttacatgtttgtgcttctcacaaaaataataataccaagcacatgttccaaatgatt
attaataattttgaggtgtttttcaaccaacttatatactttcatagttctaaaaaaacc
gtatatatggttaactctaacaaaaacttatatatgttttctctctaatacagGGAGTGT
                                                              G  S  V TCTTGGAATGGAAAATTGGGTCCGTATTACTTTTGCCTGCGTTCCATCTTCTCTTCAAGA
  L  G  M  E  N  W  V  R  I  T  F  A  C  V  P  S  S  L  Q  D TGGACTCGAAAGGGTCAAATCATTCTGTCAAAGGAACAAGAAGAAGAATTCTATAAATGG
  G  L  E  R  V  K  S  F  C  Q  R  N  K  K  K  N  S  I  N  G TTGTTAGTTGTACACACCCCTAGTTGTACATCTGACTGAAGCTGTAAATCATTTCTAGTT  9600
  C  *
ATCCCCATTTATATATTTCAATAAAACATATTGTAATGGTTCTGTTGTAGCTGTCCAAGT

CATGTACTCTACTTTTTGATGTATTTGGCCTCATTGCCTTGCATCAGTTTCAATAAAAAT

GGTTGTGTACACaatgatgatgtagaggcgaggtgttttgaccacctttttcaacaaaaat ctatatctttcaacaaatgaaaccttgagttcccttttgagtagaagtcaacatactcctt
gaatatgctatggtttccatggtctggatgaaacatgatgaatagaagtgaagttatatc
catgtcaaagttttttaatgtttaatttcattatgagaactttgatattacttctagcac
acattctctgaagtaattgtcagtttggtacttgaagggacctatattttcctattggg
ggggggggtgaataggcggtttataaccaattgtatatttgagaatatcttaatgtgga
attaaactaggtgaatatttttccaataagggtgcttttattgactcacaatgtacca
tcaagggatacaatcataatgagtacacaatcgacatctacataatcaggttgcatacgg  10200
ccaacacacacacacgcacacacacattcacacacacaaatcatgctgacgaagagcgaa
gtcatacaagatcaaaactatgcctaggcggaggaagaatagaaaaacatgaagaaatga
aaaaccgtgactgacaacatactgaccatcgacgacaaacatctgtagacaacacaaaaa
ctgcgagaaaagttctataaaactggcgccttcgagaaggaaacgacgtgcaagagttgc
catcatcggatccaaccactaaggtcatatcctgggttttcatcctgaagatcaaatccg
agcaaactccgagtaatgtctttattagggtaacgattcaaaaaatgccacaatcatgag

FIG. 10G

```
ttatgaccaattagaccagacctaggattttta tccaaagctcgagacgggtactctaga
agtaccatccaattgaagtcatcccacttgcctcaatacaaatagttgcatagatgcacg
gtccatatggcgagtaatggacatgagcgcgcatgtgtaggttaacgtgacgtgacaaga
gcctgtcgccaccactcgacgaagtgtttgatggggaggaagaagtatggctccaccaac   10800
atcccaagtttgaaacattctagagcccct taccatactcacaaagcgacaattgatgac
tatctgtatcagacgacaaatccatgtccgtcactcgctctatcttggtcattgacatac
tacctggcaaaggcggattcaagccccagacagcctgggcggccgc
```

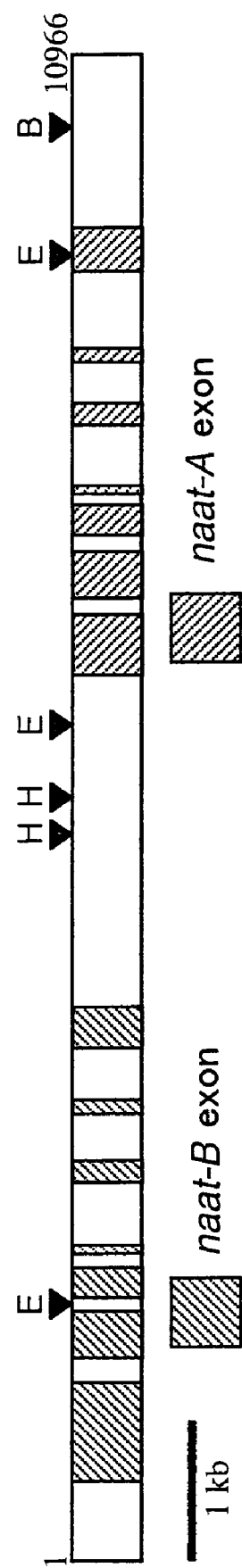

F I G. 1 3

MVHQSNGHGEAAAAAANGKSNGHAAAANGKSNGHAAAAAVEWNFARGKDGILATTGAKNS
IRAIRYKISASVEESGPRPVLPLAHGDPSVFPAFRTAVEAEDAVAAALRTGQFNCYAAGV
GLPAARSAVAEHLSQGVPYKLSADDVFLTAGGTQAIEVIIPVLAQTAGANILLPRPGYPN
YEARAAFNKLEVRHFDLIPDKGWEIDIDSLESIADKNTTAMVIINPNNPCGSVYSYDHLA
KVAEVARKLGILVIADEVYGKLVLGSAPFIPMGVFGHIAPVLSIGSLSKSWIVPGWRLGW
VAVYDPTKILEKTKISTSITNYLNVSTDPATFVQEALPKILENTKADFFKRIIGLLKESS
EICYREIKENKYITCPHKPEGSMFVMVKLNLHLLEEIHDDINFCCKLAKEESVILCPGSV
LGMENWVRITFACVPSSLQDGLERVKSFCQRNKKKNSINGC*

F I G. 1 4

ATVRQSDGVAANGLAVAAAANGKSNGHGVAAAVNGKSNGHGVDADANGKSNGHGVAADAN
GKSNGHAEATANGHGEATANGKTNGHRESNGHAEAADANGESNEHAEDSAANGESNGHAA
AAAEEEEAVEWNFAGAKDGVLAATGANMSIRAIRYKISASVQEKGPRPVLPLAHGDPSVF
PAFRTAVEAEDAVAAALRTGQFNCYPAGVGLPAARSAVAEHLSQGVPYMLSADDVFLTAG
GTQAIEVIIPVLAQTAGANILLPRPGYPNYEARAAFNRLEVRHFDLIPDKGWEIDIDSLE
SIADKNTTAMVIINPNNPCGSVYSYDHLSKVAEVAKRLGILVIADEVYGKLVLGSAPFIP
MGVFGHITPVLSIGSLSKSWIVPGWRLGWVAVYDPRKILQETKISTSITNYLNVSTDPAT
FIQAALPQILENTKEDFFKAIIGLLKESSEICYKQIKENKYITCPHKPEGSMFVMVKLNL
HLLEEIDDDIDFCCKLAKEESVILCPGSVLGMANWVRITFACVPSSLQDGLGRIKSFCQR
NKKRNSSDDC*

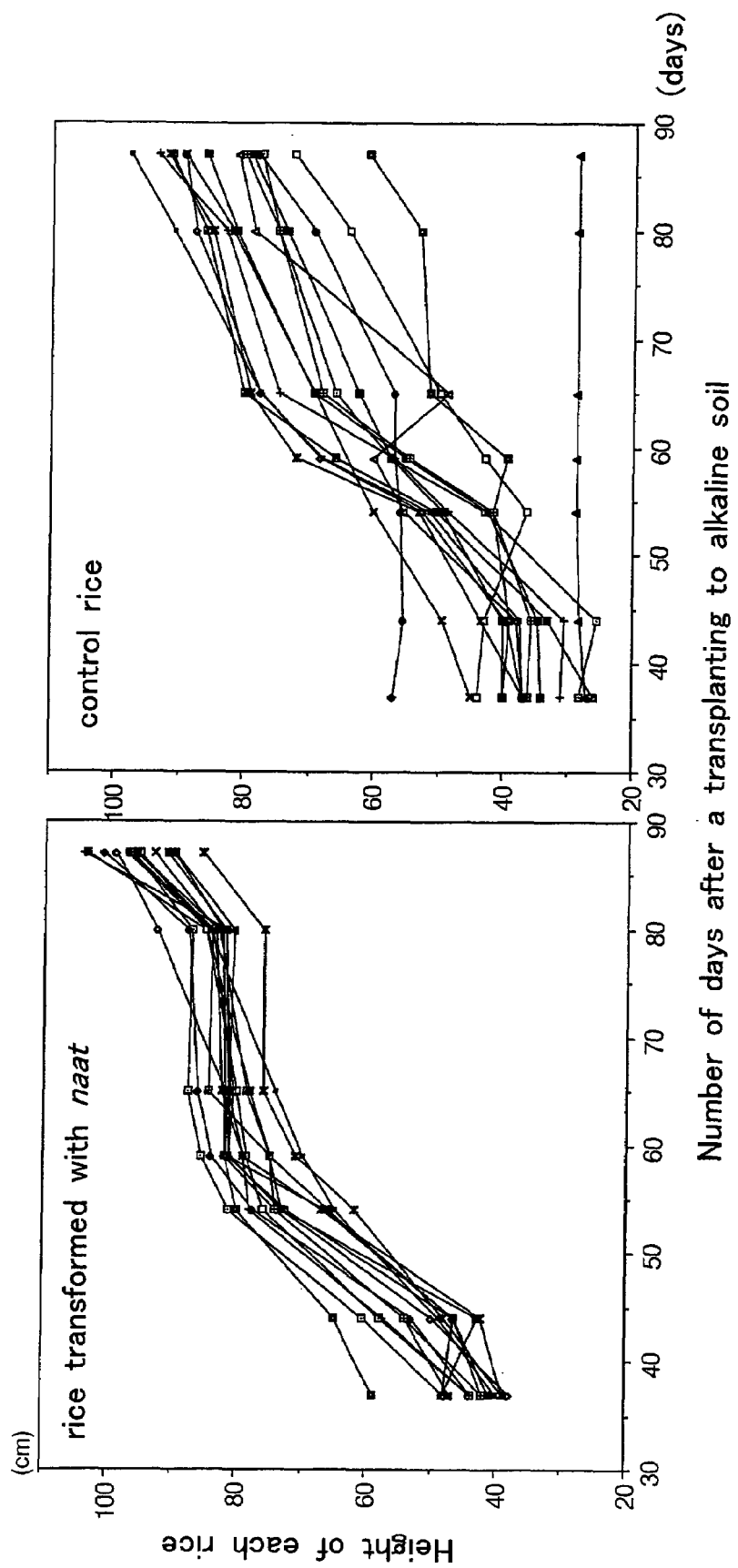
F I G. 16

METHODS OF PRODUCING TRANSGENIC GRAMINEAE PLANTS HAVING RESISTANCE TO IRON DEFICIENCY

TECHNICAL FIELD

The present invention relates to a manufacturing method for gramineae that have an iron deficiency resistance, gramineae obtained through the method, the method of growing said gramineae and the crop obtained through the method.

More specifically, the present invention relates to the creation of gramineae having an iron deficiency resistance by introducing genes, in which the gene codes an enzyme along the mugineic acid synthesizing route for gramineae, and more preferably, where said enzyme is nicotianamine amino transferase.

BACKGROUND ART

90% of the soil on the earth is inadequate soil that has some kind of problem. The inadequate soil, in general, lacks the elements essential to the growth of plants qualitatively and quantitatively, and therefore, the growth of plants is hindered or growth disorders occur due to the soil containing a large amount of heavy metals. Representative of inadequate soil is dryland salt accumulated soil. Of this type, there are ones in which NaCl and $Na_2CO_3$ are accumulated or $CaCO_3$ or $CaSO_4$ are accumulated in the topsoil due to artificial over-irrigation or dry weather over a long period of time. The halomorphic soil causes a salt density disorder, and the calcareous soil causes an iron deficiency disorder.

Approximately 30% of the cultivated soil on the earth is said to be a potentially iron deficient area. (Wallence et al. "Iron Chlorosis in Horticultural Plants," 75 American Society for Horticultural Science, 819–839 (1960)). The calcareous soil in semiarid areas has calcareous components eluted from the core material due to a capillary effect and it is accumulated on the surface of the ground. In this soil, the pH is increased and becomes alkaline, and therefore, the iron in the soil exists in the form of $Fe(OH)_3$ and has extremely low solubility.

The plants grown in these soils have iron deficient chlorosis due to little soluble iron, and their growth is hindered or they die.

The iron obtaining system of higher plants is classified into two types, Strategy I and Strategy II. Strategy I is an iron obtaining system for higher plants excluding gramineae. It is a system in which the insoluble trivalent iron in the soil is reduced by the trivalent iron reduction enzyme that is present on the surface of the cell on the root, and then is it absorbed by the divalent iron transporter. Of those plants that have this system, there are ones that have a system to emit protons in the rhizosphere to increase the activity of the trivalent iron reduction enzyme by lowering the pH in the rhizosphere, and ones that have a system to emit phenol compounds in the rhizosphere and supply the Fe (III) to the trivalent reduction enzyme that is present on the surface of the cell by an Fe (III)-phenol compound chelate. Recent studies have isolated the divalent iron transporter IRT1 (Eide et al., "A novel iron-regulated metal transporter from plants identified by functional expression in yeast," 93 Proc. Natl. Acad. Sci. 5624–5628 (May 1996)) that distinctively emerges on the root of the *arabidopsis thaliana*, and the gene for the trivalent reduction enzyme of the *arabidopsis thaliana*. (Robinson et al., "The froh gene family from *Arabidopsis thaliana*: Putative iron-chelate reductases", 196 Plant and Soil 245–248, Kluwer Academic Publishers (1997)).

Strategy II is an iron obtaining system that is only observed in gramineae, which is one of the monocotyledons. The gramineae emits mugineic acids that have trivalent iron chelate activity under iron deficient conditions, and absorbs iron from the root as an "Fe (III)-mugineic acid" complex. (Takagi et al., "Physiological aspect of magineic acid, a possible phytosiderophore of graminaceous plants," 7(1–5) Journal of Plant Nutrition 469–477 (1984)). There are 7 mugineic acids (MAs) that are known: mugineic acid (MA), 2'-deoxymugineic acid (DMA), 3-hydroxymugineic acid (HMA), 3-epihydroxymugineic acid (epiHMA), avenin acid (AVA), distichon acid and epihydroxydeoxymugineic acid (epiHDMA). All of the mugineic acids (MAs) are, as shown in FIG. 1, synthesized with methionine as a precursor. (Shojima et al., "Biosynthesis of Phytosiderophores", 93 Plant Physiol. 1497–1503 (1990) and Ma et al., "Biosynthesis of Phytosiderophores in several Triticeae species with different genomes," Vol. 50, No. 334, pp. 723–726, Journal of Experimental Botany, (1999)).

The excretion of mugineic acid has a circadian rhythm (Takagi et al. supra) and its excretion reaches a maximum after sunrise, and there is no excretion during the night. In addition, it has been observed that the granule expands before the excretion in iron deficient barley root and wilts after the excretion (Nishizawa et al., "The particular vesicle appearing in barley root cells and its relation to mugineic acid secretion," 10(9–16) Journal of Plant Nutrition 1013–1020 (1987)). Therefore, it is believed that the mugineic acid is synthesized in this granule. These fact indicates that the responding of the gramineae to the iron deficiency is formed by not only the synthesis of the mugineic acid but also is formed by a complicated system such as the transmission of an iron deficiency signal and changes in the root form.

It has been reported that a gene for the nicotianamine synthesizing enzyme, which is an enzyme related to the mugineic acid synthesizing route, has been isolated and it is induced by an iron deficiency. (Higuchi et al., "Cloning of Nicotianamine Synthase Gene, Novel Genes Involved in the Biosynthesis of Phytosiderophore," 119 Plant Physiology 471–479 (February 1999)). In addition, the gene for nicotianamine amino transferase (NAAT) has been isolated and it is induced by an iron deficiency. (Takahashi et al., "Purification, characterization and DNA sequencing of nicotianamine aminotransferase (NAAT-III) expressed in Fe-deficient barley roots," Plant nutrition, 279–280, Kluwer Academic Publishers (1997))

Moreover, through differential screening using mRNA extracted from an iron deficient barley root and a control barley root, genes Ids1, Ids2, and Ids3 which were specifically induced under iron deficient conditions have been isolated. The Ids1 is a gene that codes for metallothionain protein. (Okumura et al., "An iron deficiency-specific cDNA from barley roots having two homologous cysteine-rich MT domains," 17 Plant Molecular Biology 531–533, Kluwer Academic Publishers (1991)). Ids2 is a gene in which the sequence of amino acids that is assumed from its genetic sequence is homologous to the hydroxide enzyme. (Okumura et al., "A dioxygenase gene (Ids2) expressed under iron deficiency conditions in the roots of *Hordeum vulgare*", Plant Molecular Biology 25; 705–719, Kluwer Academic Publishers, (1994)) Ids3 is also a gene in which the sequence of amino acids that is assumed from its genetic sequence is homologous to the hydroxide enzyme. (Nakanishi et al., "Expression of a Gene Specific for Iron Deficiency (Ids3) in the Roots of *Hordeum Vulgare*", 34(3) Plant Cell Physiol 401–410, JSPP (1993)) There are two hydroxide reactions along the epihydroxymugineic acid synthesizing route, and this gene is believed to code the enzyme that catalyzes this reaction.

In addition, the examples of proteins that are induced by an iron deficiency of the barley root are, the IDS3 protein, adenin-ribose-phosphate transferases (Itai et al., "Induced activity of adenine phosphoribosyltransferase (APRT) in iron-deficient barley roots: a possible role for phytosiderophore production". Vol. 51, No. 348, pp. 1179–1188, Journal of Experimental Botany (July 2000)), formicacid dehydrogenate enzyme (Suzuki et al., "Form ate Dehydrogenase, an Enzyme of Anaerobic Metabolism, is induced by Iron Deficiency in Barley Roots," 116 Plant Physiol 725–732 (1998)), and 36 kDa protein (Tomohiro Irifune, "Partial amino acid sequences of a specific protein in iron-deficient barley roots", (1991)). Gramineae biosynthesizes mugineic acid under iron deficient conditions. This time, it is believed that the methionine contained in the root is reduced so that methionine is synthesized during a methionine cycle and at the same time, in order to convert the generated adenine into AMP, adenine-ribose-phosphate transferases are induced. (Itai et al., supra)

The formic acid dehydrogenate enzyme decomposes formic acid generated during the methionine cycle. It was reported that the root of a gramineae with an iron deficiency has a deformation of the mitochondrion and a reduction of the energy charge of the electron transmission system (Mori et al., "Why are young rice plants highly susceptible to iron deficiency", Iron nutrition and interactions in plants, 175–188, Kluwer Academic Publishers (1991)). It is believed that the formic acid dehydrogenate enzyme is induced by the anaerobic condition generated by the iron deficiency, and that NADH is supplied as an energy source.

Along with the increase in population, an increase in food production is a significant issue as a condition for human existence in the future. Gramineae has been one of the most important foods since ancient times, however, in reality, the growth of gramineae is difficult in areas with iron deficiencies. If it is possible to grow graminae in an area with an iron deficiency, an increase in food production would be possible, thus it has been attracting people's attention as one of the solutions to increase food production.

DISCLOSURE OF THE INVENTION

The present invention has as an objective to provide gramineae with iron deficiency resistance, which can be grown in areas with iron deficiencies.

More specifically, the present invention has as an objective to provide graminae with an iron deficiency resistance that vigorously grows even in a calcareous alkaline soil by introducing the gene of an enzyme in the biosynthesis of the mugineic acid of gramineae to the gramineae.

The present invention relates to a manufacturing method for graminenae with improved iron absorbency by introducing a gene that codes an enzyme on the mugineic acid biosynthesis route to the gramineae. and more specifically, a gramineae with improved iron absorbency through the introduction of the gene naat, wherein said enzyme is nicotianamine amino transferase (NAAT).

In addition, the present invention relates to the gramineae which can be manufactured by the method indicated above. Specifically, the present inventrion relates to the gramineae with improved iron absorbency by introducing a gene that codes an enzyme on the mugineic acid biosynthesis route to the gramineae, more specifically, the gramineae with improved iron absorbency through the introduction of the gene naat that codes the enzyme, wherein said enzyme is nicotianamine amino transferase (NAAT).

Furthermore, the present invention pertains to a growing method of said gramineae with improved iron absorbency and crops obtained through said growth.

BRIEF DESCRIPTION OF DRAWINGS

The patent or application file contains at least one photograph executed in color. Copies of this patent or patent application publication with color photograph(s) will be provided by the Office upon request and payment of the necessary fee.

FIG. 4 shows the result of measurement of NAAT activity in a root cultivated in a hydroponic solution in the presence of iron (+Fe) and an iron deficiency (−Fe). In FIG. 4, the whited out portion shows the case for +Fe and the shaded portion shows the case of −Fe. WT shows an autochthon type and 1-5, 1-6 and 1-7 show transformants.

FIG. 7 shows a restriction map of a phage DNA including an isolated genome naat. In FIG. 7, E indicates EcoRI, H indicates HindIII, B indicates BamHI, and N indicates NotI. The NotI site on both sides is the NotI located at the arm of λFIXII.

In FIG. 8, NPTII is a kanamycin resistant gene, HPT is a hygromycin resistant gene, GUS is a β glucuronidase gene with intron, LacZ is a β galactosidase gene, 35P is a 35S promoter, NP is an NOS promoter, NT is an NOS terminator, MCS is a multi-cloning site, and Riori is an Ri plasmid replication starting point.

FIGS. 9A through 9D show the base sequence (SEQ. ID No. 3) of the obtained genome naat.

FIGS. 10A through 10G show the base sequence of naat (SEQ. ID No. 3) and 5' upstream of naat-A and naat-B, the exon, the intron and 3' downstream, which were determined by comparing with the cDNA. In FIGS. 10A through 10G, the uppercase letters show the exon portion that is a transcription on the cDNA (SEQ. ID No. 1 and 2) and the lowercase letters show the rest.

FIG. 11 is a schematic view of the obtained genome fragment. In FIG. 11, E is EcoRI, H is HindIII and B is BamHI.

FIG. 13 shows an amino acid expressed in a single letter code of an amino acid sequence of NAAT-A (SEQ. ID No. 1) estimated from the cDNA.

FIG. 14 shows an amino acid expressed in a single letter code of an amino acid sequence of NAAT-B (SEQ. ID No. 2) estimated from the cDNA.

FIG. 16 is a graph that shows the transition of the height of each gramineae in which a genome naat was introduced after being transplanted to alkaline soil. In FIG. 16, the gramineae on the left is the one transformed with genome naat and the one on the right is the control gramineae in which only the vector was transplanted.

BEST MODE FOR CARRYING OUT THE INVENTION

Said Strategy II, which is an iron obtaining system observed only in gramineae, from among the monocotyledon, utilizes a method of biosynthesizing and emitting mugineic acids to obtain iron. Therefore, the enhancement method of enzymes along the biosynthesis route of mugineic acids (see FIG. 1) was investigated.

The present inventors first paid attention to nicotianamine amino transferase (NAAT) as the enzyme on the mugineic acid synthesizing route, and then attempted to introduce the gene naat. Miraculously, it was found that gramineae with the gene introduced were able to vigorously grow even in a calcareous alkaline soil.

Figure 2:
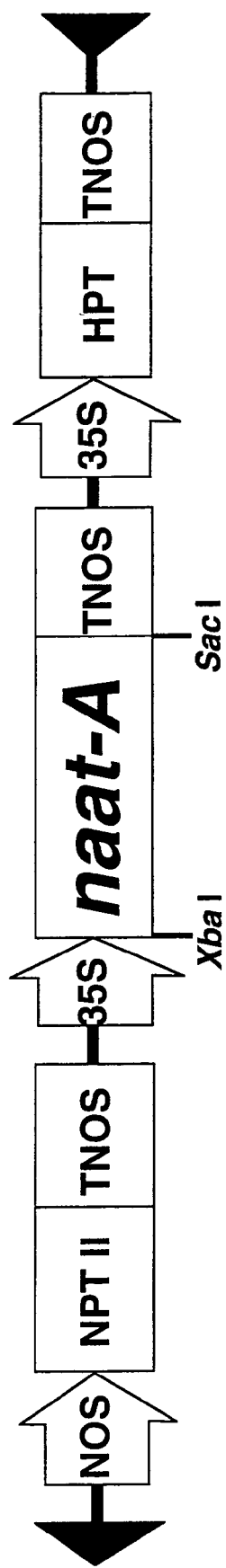
FIG. 2 shows the genetic sequence of the binary vector pIG121Hm for a gramineae transformation in which the cDNA of naat-A is inserted.

The cDNA of the naat-A, the nicotianamine amino transferase (NAAT), was integrated into pIG121Hm using the XbaI and SacI portion and the binary-vector shown in FIG. 2 was created. The obtained vector was used for transformation by introduction into an agro-bacterium.

The transformation of the gramineae was carried out in accordance with the method by Hiei et al., "Efficient transformation of rice (*Oryza sativa* L.) mediated by *Agrobacterium* and sequence analysis of the boundaries of the T-DNA", 6(2) The Plant Journal 271–283, (1994), and "Tsukinohikari" was used as the material. The callus induced from the blastoderm was immersed and infected in said transformed agro-bacterium suspension solution, and a regenerator (T1 plant) was obtained. Then, finally, the 34 strain transformed gramineae was obtained from seed.

Figure 3:
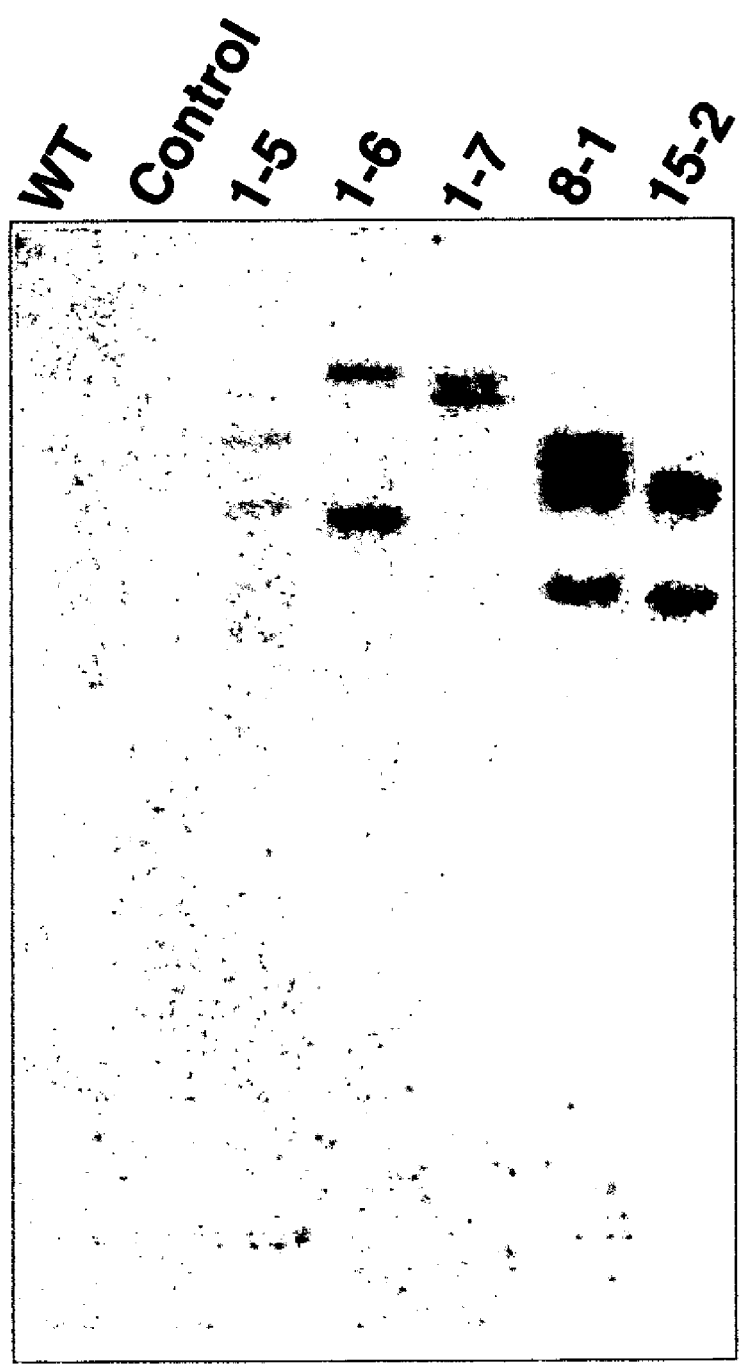
FIG. 3 is a photo in place of a drawing that shows the results when detection of the introduced gene is carried out by the Southern Hybridization method. WT in FIG. 3 shows a case of an autochthon gramineae, and the control shows a control gramineae in which only the vector was introduced. 1-5, 1-6, 1-7, 8-1 and 15-2 show transformants having a 35S promoter.

The introduced gene was detected by the Southern Hybridization method. The results are shown in FIG. 3. In FIG. 3, WT shows a case of an autochthon gramineae and the control shows a case of a gramineae in which only the vector was introduced. 1-5, 1-6, 1-7, 8-1 and 15-2 show the transformer, which has a 35S promoter. As shown in FIG. 3, all the transformers have an over-generation of naat-A. In addition, it was found that among those 35S transformed gramineae, 8-1 and 15-2 had at least 5 copies and 2 copies of naat introduced, respectively.

By introducing the genetic naat, it is assumed that compared to the autochthon and one in which is it only introduced on the vector, there is an over-emission of nicotianamine amino transferase (NAAT) and as a result, the mugineic acid synthesizing route is activated, and consequently, the mugineic acids which are required for iron intake was massively produced.

Therefore, first, the NAAT activity of these species was investigated. Young plants (T2), 3 weeks after sprouting, were cultivated for 2 weeks in a hydroponic solution with the presence of iron (+Fe) and an iron deficiency (−Fe). The results of measurement of NAAT activity is shown in FIG. 4. In FIG. 4, the whited out portion shows the case of +Fe and the shaded portion shows the case of −Fe. WT shows the autochthon type and 1-5, 1-6 and 1-7 show the transformers.

As a result, for both +Fe and −Fe, the transformed ones had higher relative activity than the non-transformed autochthon one (WT), and in addition, it was found that the relative activity further increased with the −Fe condition. This shows that not only the introduction of a gene allows the high activity of NAAT, but also, the transformer is significantly promoted with NAAT activity in the presence of an iron deficient state or conditions with an insoluble iron. In other words, it is assumed that it has become a species with a strong resistance to an iron deficient condition or the condition of insoluble iron.

Figure 5:
FIG. 5 is a photo in place of a drawing that shows the growing state of each gramineae which is 8 weeks after a transplanting to alkaline soil. The control in FIG. 5 shows the control gramineae in which only the vector is transplanted and the gramineae on the right is the one that is transformed.
Figure 6:
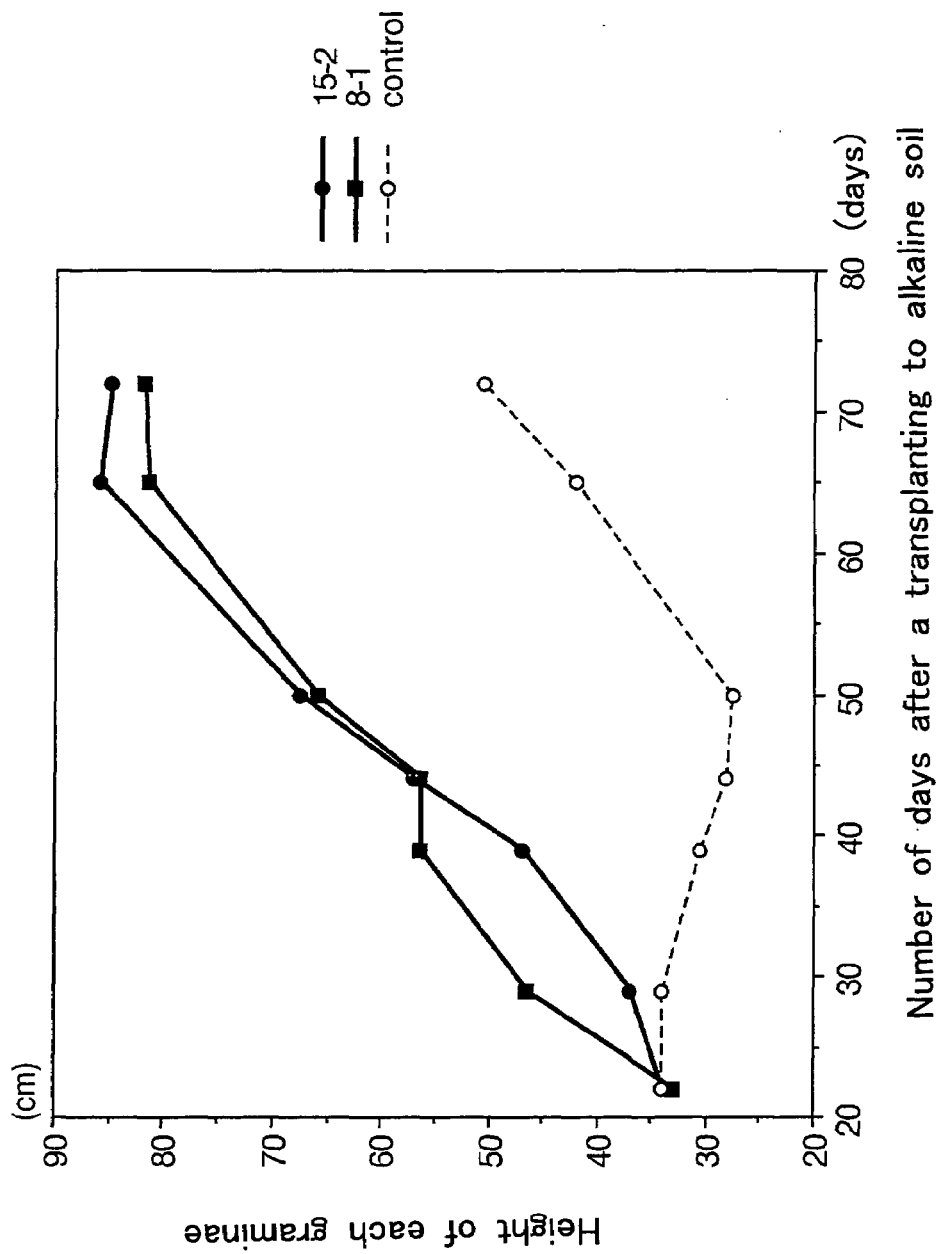
FIG. 6 is a graph that shows a transition of the height of each gramineae after being transplanted to alkaline soil. A black dot shows the transformer 15-2, a black square shows the transformer 8-1, and a white dot shows the control gramineae in which only the vector was transplanted.

From the above, it was found that the introduction of a gene naat promotes NAAT activity. Nonetheless, whether these transformers can be grown in actual iron deficient soil was investigated. When 35S-naat-A transformed gramineae was transplanted to an alkaline soil in the condition of insoluble iron, its leaves turned yellow up to 2 weeks after the transplant, however, after 4 to 5 weeks, the new leaves became a dark green and started to recover. FIG. 5 is a photo showing the growth state 8 weeks after it was transplanted to alkaline soil. In FIG. 5, the control shows the control gramineae in which only the vector was transplanted and the gramineae on the right shows the transformed one. It is found in comparison to the control one, that the transformed one has significantly superior growth. In addition the transition of the plant height after it was transplanted to the alkaline soil is shown in FIG. 6. In the graph in FIG. 6, the Y axis shows the height of the plant (cm) and the X axis shows the number of days after it was transplanted to the alkaline soil. Black dots show transformer 15-2, black squares show transformer 8-1 and white dots show the control gramineae in which only the vector was transplanted.

As described above, 35S transformed gramineae 8-1 has at least 5 copies of naat genes, and 35S transformed gramineae 15-2 has at least 2 copies of naat genes introduced. From the height of the plant in FIG. 6, the number of copies of the gene is not related and it shows that as long as the gene was introduced, the gramineae has gained an iron deficiency resistance.

As described above, the introduction of the gene increases the activity of the enzyme along the mugineic acid synthesizing route of the gramineae, and furthermore, it was found that by doing so, it added an iron deficiency resistance.

Figure 1:
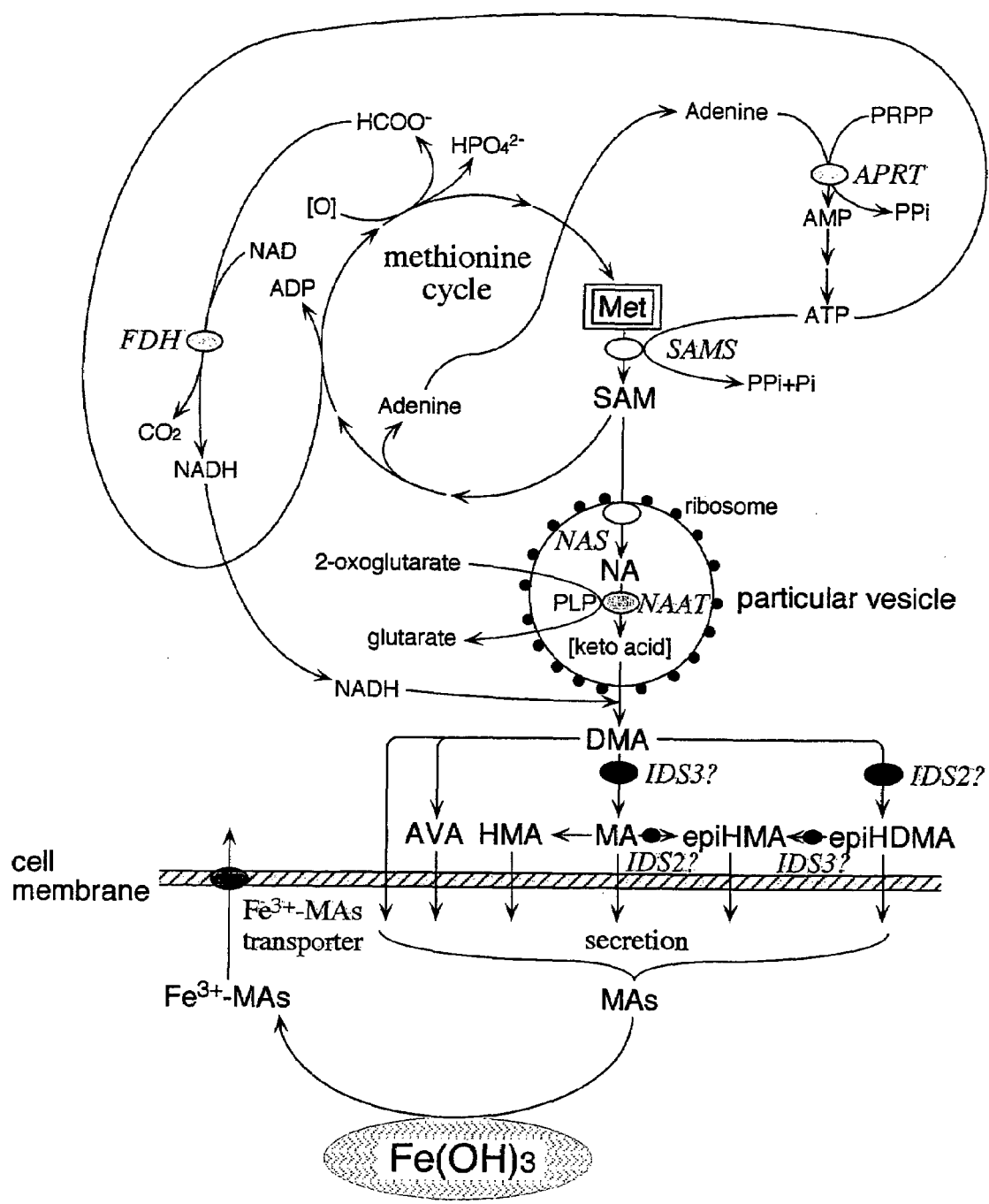
FIG. 1 shows the mugineic acids' biosynthesis route for a barley root with an iron deficiency and its rhizospheric environment.

For the enzyme along the mugineic acid synthesizing route of the present invention, it is acceptable as long as it is an enzyme along the mugineic acid biosynthesizing route shown in FIG. 1, and the introduction of the gene that codes said enzyme increases its activity. As described above, among the candidates, nicotianamine amino transferase (NAAT) and nicotianamine synthesizing enzyme are desirable. The gene that codes the enzyme along the mugineic acid synthesizing route of the gramineae of the present invention can be either cDNA or one derived from the genome. As described in the later section, the use of a genome is a preferable example of the present invention.

Therefore, for the gramineae of the present invention, it is acceptable as long as it is a plant that can absorb iron through the Strategy II system, and it is not limited to gramineae in the academic sense. The preferable examples of gramineae of the present invention are, rice plants, corn, sorghum, wheat, barley, and oats. These gramineae can have the method of the present invention applied regardless of its species, and the gramineae with the target gene introduced can be manufactured.

The promoter of the present invention is not limited as long as it can generate the target enzyme. 35S promoter, and more specifically, CaMV35S promoter can be used.

The vector of the invention is not specifically limited as long as it can preferably be used during the transformation. The transformation method of the present invention is not limited to said method that uses the agro-bacterium method and a variety of transforming methods using particle guns, etc., can be employed. The cells of the gramineae formed are not limited to the cell from said callus and a variety of cells can be used, however, normally it is preferable to use ones derived from the callus.

The iron deficiency related to the present invention can be a state where iron is deficient, but preferably it is a state where the form of the iron is one that the plant has problems absorbing, and depending on the type of plant, it can be determined whether it is deficient of iron or not. Therefore, the definition of the iron deficiency resistance in the present invention is that the resistance is to the difficult conditions where the plants of the subject have difficulty absorbing the iron in the soil.

Next the present inventor attempted an introduction of a genome naat of barley instead of the cDNA of the naat.

For the genome naat, the library (manufactured by Srtratagen Corp.) created using the genome DNA extracted from barley (*Horudeum vulgare* L. var. *Igri*) was used. This library was partially cut by restriction enzyme Sau3AI and was introduced to the XhoI site of the λFIXII vector. For the probe, the entire cDNA of the naat-A, which was isolated in advance was used. An *Escherichia coli* XL1-Blue MRA (*E. coli* XL1-Blue MRA (P2)) was used as the host.

As the result of screening, five (5) phages were obtained. From these, each of the phage DNA was isolated and a restriction map was created. It was found that the same fragments were increased for all the cases. Namely, it was found that the obtained five phages were derived from the same portion of the genome. It was assumed that it contains the naat used in the probe. Therefore, the base sequence determination for the one of them shown in FIG. 7 was carried out.

The phage DNA shown in FIG. 7 is inserted in the NotI site of the plasmid vector-pBIGRZ1 in which 10 kb or more fragments can be inserted and a transformation of the gramineae using agro-bacterium can be carried out. (See FIG. 8.)

In addition, up to 11.0 kb of the fragments shown in FIG. 7 were divide into 4 parts, that is A to D, and they were introduced to the EcoRI site (B, C) of the plasmid vector-pBluescript SK(−) or the NotI and the EcoRI site (A, D).

For fragments A to D, the base sequence was determined from both sides of the fragment using a primer based on the sequence on the plasmid (M13 forward primer, M13 reverse primer). To determine the DNA base sequence, the DNA sequencer DSQ-2000L of Shimadzu, Ltd. was used.

The details of the sequence determination are shown in the examples.

Sequence Identification No. 3 in the sequence listing shows the determined 10,966 bp base sequence. In addition, the entire sequence is shown in FIGS. 9A through 9D (without base number).

From the obtained base sequence, this 10,966 bp gene is found to be a fragment of the barley genome that codes the naat-A and naat-B that have been obtained. It was in the order of naat-B and naat-A.

5' upstream of naat-A and naat-B, the exon, the intron and 3' downstream were determined by comparing with the 10th cDNA as shown. In FIG. 10, the upper case letters show the exon portion transcribed to the cDNA, and the lower case letters show the rest. The base number of the exon portions are as follows.

Figure 12:
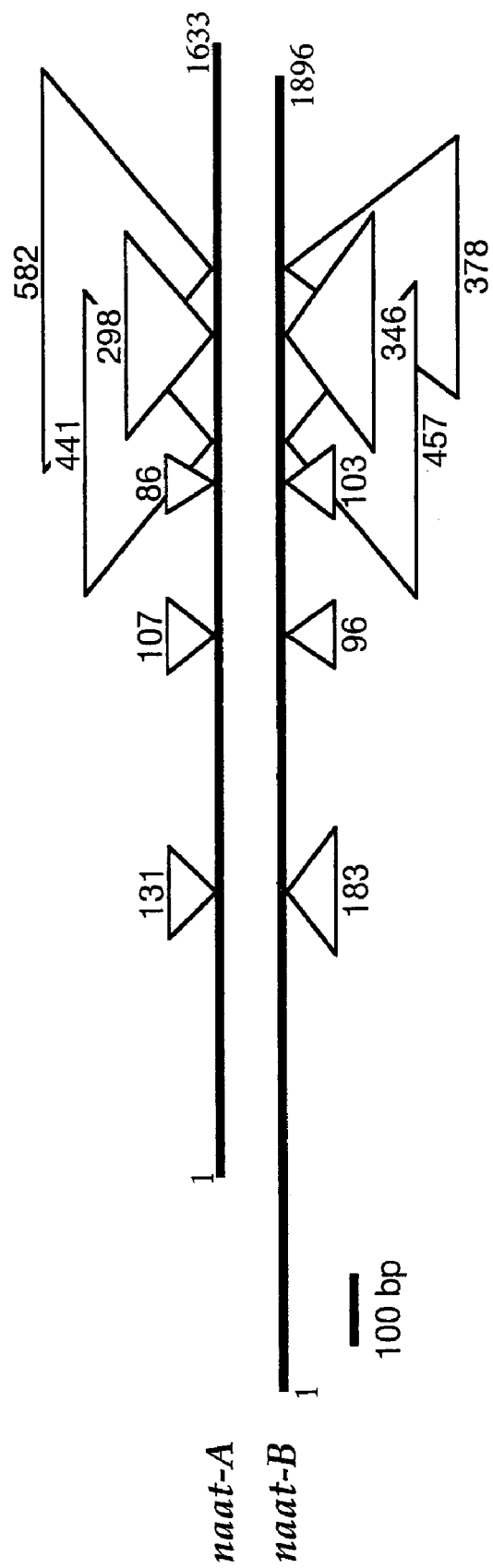
FIG. 12 shows the location and the size of the intron in the cDNA of naat-A and naat-B.

FIG. 11 shows the schematic view thereof. The exon portion is shown in the shaded portion. Both genes comprise 6 intron and 7 exon. In addition, the insertion location of the intron was homologous for each of the genes. FIG. 12 shows the location in the cDNA and what size of intron was inserted.

The amino acid sequence of naat-A and naat-B estimated from the cDNA, is shown in FIGS. 13 and 14, respectively.

The transformation method of gramineae, in which an obtained barley genome naat is introduced, was carried out in accordance with the transformation method of said 35S transformed gramineae.

Next, the inspection of the iron deficiency resistance of the gramineae introduced with the obtained genome naat was carried out. Of the obtained regenerators (T 1), 39 individuals and 15 individual controls, in which only the vector was introduced, were used, and the inspection was carried out in a similar manner to the 35S transformed plant. From the 5th week after the transplantation, the height of the plants was measured every week or every other week. Twice every 4 to 5 weeks, they were transplanted to a pot with increased soil.

The leaves of the transformed gramineae with the genome naat turned yellow by the second week after they were transplanted to the alkaline soil, however, during the 4th to 5th week, new leaves started to become dark green and recover, and then they started to show vigorous growth. Compared to this, the control group in which only the vector was introduced continued to have yellow leaves for a long period of time, and from around the 8th week, new leaves started to turn green.

Figure 15:
FIGS. 15A and 15B are photographs in place of drawings that shows the growing state of each gramineae in which a genome naat was introduced, ten (10)-weeks after being transplanting to an alkaline soil. The control in FIGS. 15A and 15B shows the control gramineae in which only the vector is transplanted and the gramineae on the right is the one that is transformed with a genome naat.
Figure 15:
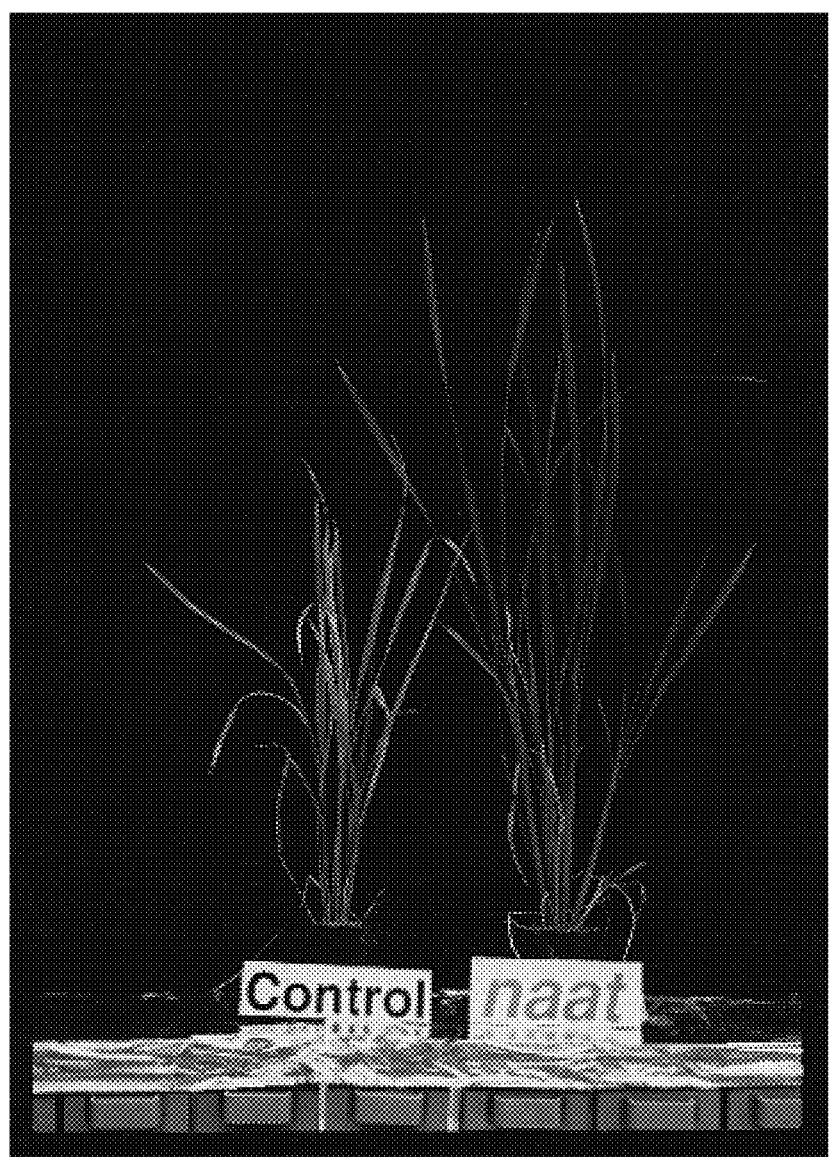

FIG. 15 is a photo that shows the growth state of $10^{th}$ week after it was transplanted to the alkaline soil. The control in FIG. 15 shows the control gramineae in which only the vector was transplanted. The gramineae on the right is the one transformed with the genome naat.

FIG. 16 shows the transition of the plant height after it was transplanted to the alkaline soil. In the graph of FIG. 16, the Y axis shows the plant height (cm), and the X axis shows the number of days after it was tranplanted to the alkaline soil. In FIG. 16, the gramineae on the left shows the gramineae transformed with a genome naat and the one on the right shows a control gramineae in which only the vector was transplanted.

From the above, it was found that the introduction of the genome naat allows the gramineae to have additional iron deficiency resistance.

EXAMPLES

The present invention is described in detail using examples as follows, however, the present invention is not limited to these.

Example 1

Transforming Method of Gramineae in which there is an Over-Developing Naat with CaMV35S Promoter The binary vector shown in FIG. 2 was created by integrating the cDNA of the genetic naat to pIG121Hm, using the XbaI and SacI portions. These were introduced to agrobacterium and used for the transformation.

The transformation of gramineae was carried out in accordance with the method of Hiei et al., "Efficient transformation of rice (*Oryza sativa* L.) mediated by *Agrobacterium* and sequence analysis of the boundaries of the T-DNA", 6(2) The Plant Journal 271–283, (1994) and "Tsukinohikari" was used as the material. First, hulled seeds were sterilized and seeds on a callus-inducing medium (pH 5.8) comprising N6 inorganic salt, 30 g/L of N6 vitamin, 2 mg/L of sucrose, 2, 4-D, and 2 g/L gelrite were cultured for 3 weeks at 25° C. under the conditions of 60 µmol/m$^2$s with a 16-hour photo period/8 hour dark period, and the callus was induced from the blastoderm.

After it was transplanted to the new medium and cultured for 3 days at 25° C. in a bright place, it was immersed in the agro-bacterium suspension with an agro-bacterium suspension medium (pH5.8) (20 g/L of AA inorganic salt, amino acid, B5 vitamin, 2 mg/L of sucrose, 0.2 mg/L of 2, 4-D, 10 mg/L of kinetin and acetosyringone). Then after it was dried with a paper towl, it was infected for 3 days at 28° C. in a dark place in the co-existing culturing medium (pH5.2) (30 g/L of N6 inorganic salt and N6 vitamin, 10 g/L of sucrose, 2 mg/L of glucose, 10 mg/L of 2, 4-D, and 2 g/L of acetosyringone gelrite).

Then, the agro-bacterium was removed by rinsing the callus with a sterilized washing solution with 500 mg/L of Claforan, and it was placed on a selected medium containing 50 mg/L of hygromycin (pH5.8) (30 g/L of N6 inorganic salt and N6 vitamin, 2 mg/L of sucrose, 2 g/L of 2, 4-D, 500 mg/L of gelrite, 50 mg/L of Claforan and hygromycin) and cultured for 3 weeks at 25° C. in a bright place.

After it was cultured, it was transferred to a redifferentiation medium (pH5.8) (30 g/L of MS inorganic salt and MS vitamin, 30 g/L of sucrose, 2 g/L of sorbitol, 1 mg/L of casamino acids, 2 mg/L of NAA, 500 mg/L of BAP, 50 mg/L of Claforan, 4 g/L of hygromycin and gelrite) and the regenerator (T1 plant) that was redifferentiated in 3 to 5 weeks was transferred to an inspection medium. The inspection medium (pH5.8) comprises 30 g/L of MS inorganic salt and MS vitamin, 50 mg/L of sucrose, 8 g/L of hygromycin, and agar.

The plants that grew to fill the petridish were established for 4 to 5 days, transferred to a soil mixed with a synthetic culture soil (BONSOL 1, Sumitomo Chemical Co., Ltd.) and Vermiculite in a 1:1 ratio and seeds were obtained. Consequently, a 34 strain transformed gramineae was obtained.

Example 2

Detection of the Introduced Gene Using the Southern Hybridization Method

The leaves of the T1 plant obtained in Example 1 were ground and the genome was extracted by a modification of the C-TAB method. The extracted genome was treated with Hind III and separated by electrophoresis using a 0.8% agarose gel. These were blotted on a nylon membrane. Using the primer created with the internal sequence of the naat on a probe, and one labeled with $^{32}$p by PCR, hybridization was carried out. Then the band was detected using BAS 2000 (Fuji Photo Film Co., Ltd.).

The results of this Southern Hybridization are shown in FIG. 3. In FIG. 3, WT shows the autochthon gramineae, and the control shows a control gramineae in which only the vector was introduced. 1-5, 1-6, 1-7, 8-1 and 15-2 are cases in which the gramineae has an over-emergence of naat-A with the 35S promoter.

From the results shown in FIG. 3, it was found that of the 35S transformed gramineae, at least 5 copies and 2 copies of naat were introduced to the 8-1 and 15-2, respectively.

Example 3

Inspection of Iron Deficiency Resistance Using Alkaline Soil

As a sample soil, a fossil shell soil comprised of the following composition was used.

The content of each element is shown as % dry soil after analysis by several methods, dry weight method after ashing, flame photometry, atomic absorption, spectrophotometry and etc. Some elements were shown as chemical compounds. Therefore, summing up all data covers more than 100% because some elements were doubly counted.

| | |
|---|---|
| Water content | 0.48% |
| Total phosphate | 0.12% |
| Total potassium | 0.12% |
| Total silicate | 22.79% |
| Total lime | 37.82% |
| Total magnesia | 0.91% |
| Total manganese | 0.018% |
| Total boron | 0.003% |
| Alkaline | 38.80% |
| Hydrochloride insoluble substance | 28.88% |
| Iron oxide | 0.99% |
| Aluminum oxide | 5.59% |
| Zinc | 0.002% |

The soluble iron content of this soil was 2.2 ppm, the pH was 8.78 and the electric resistance was 0.03 mΩ.

The inspection of the 35S transformed plant was carried out such that, first, the obtained seeds from the regenerator (T1) of the transformed plant were sown on an MS solid medium containing 50 mg/L and selected, and after they were established, young plants (T2) that grew to 20 to 25 cm were used.

The inspection of the resistance was carried out for 16 of the 34 strains having 27 species. The inspection method is as follows: first, a paper towel and a filter were cut in a circle and placed on the bottom of a plastic black pot (0.5 L) and filled with alkaline soil. Plants were transferred to the pot and then from the bottom of the pot placed in a hydroponic solution (Kasugai Solution: $7 \times 10^{-4}$M $K_2PO_4$, $1 \times 10^{-4}$M KCl, $1 \times 10^{-4}$M KH$_2$PO$_4$, $2 \times 10^{-3}$M Ca(NO$_3$)$_2$, $5 \times 10^{-4}$M MgSO$_4$, $1 \times 10^{-5}$M H$_3$BO$_3$, $5 \times 10^{-7}$M MnSO$_4$, $5 \times 10^{-7}$M ZnSO$_4$, $2 \times 10^{-4}$M CuSO$_4$, $1 \times 10^{-8}$M (NH$_4$)$_3$MoO$_{24}$, $1.5 \times 10^{-4}$M Fe-EDTA) at 2 to 3 cm from the bottom of the pot, and grown in a greenhouse at a temperature of 30° C. during the day and 25° C. at night. The alkaline soil was increased to 1 L after 3 to 4 weeks and after 8 to 9 weeks, increased to 2 L and transferred. From the second week after the transplantation, the plant height was measured every week or every other week.

The measurement of the NAAT relative activity of the transformed gramineae (35S-naat gramineae) grown in the hydroponic solution of +Fe (iron presence) or −Fe (iron deficiency) was carried out as follows. Young plants (T2), 3 weeks after the sprouting, were grown with an +Fe and −Fe hydroponic solution for 2 weeks, and the NAAT activity at the root of each plant was measured. The results are shown in FIG. 4. In FIG. 4, the whited out portion shows the case for +Fe, and shaded portion shows the case for −Fe. WT shows the autochthon case and 1-5, 1-6 and 1-7 show the transformed cases.

In both the +Fe and −Fe case, the transformed one had a higher relative activity than the non-transformed autochthon (WT) and the relative activity was even higher in the case of −Fe. (See FIG. 4)

Example 4

Inspection of Iron Deficiency Resistance Using Alkaline Soil 35S-naat-A transformed gramineae were transferred to an alkaline soil and their growth was observed.

The leaves of the 35S-naat-A transformed gramineae turned yellow until the second week after the transplant, however, on the 4th to 5th week, the new leaves turned to a deep green and recovered. Thus it was found that the introduction of naat allows the gramineae to have an iron deficiency resistance.

FIG. 5 is a photo showing the growth state at 8 weeks after the transplant to the soil. In FIG. 5, the control shows the control gramineae in which only the vector was transplanted. The gramineae on the right is transformed.

FIG. 6 shows the transition of the plant height after being transplanted to the alkaline soil. In the graph of FIG. 6, the Y axis shows the plant height (cm) and the X axis shows the number of days after it was transplanted to the alkaline soil. Black dots show transformer 15-2, black squares show transformer 8-1 and white dots show the control gramineae in which only the vector was transplanted.

It was found that by introducing a gene naat, an iron deficiency resistance could be added to the gramineae. (See FIGS. 5 and 6.)

Example 5

Isolation of Naat-A and B Genomic Clone

The screening procedure was carried out in accordance with Itaru Watanabe, "*Cloning and Sequence*", Nosonbunka (1989).

The λ FIXII library purchased from Srtratagene Corp. was used as the library. This is created using genome DNA extracted from barley (*Horudeum vulgare* L. var. *Igri*). The genome DNA was partially cut by the restriction enzyme Sau3AI, and introduced to the XhoI site of the λ FIXII vector. The insertion size of the library was 9 to 23 kb.

(1) *E. coli* (XL1-BLUE MRA (P2)) was cultured overnight in a NZCYM liquid medium, (10 g of NZ amine, 5 g of NaCl, 1 g of casamino acid, 5 g of Bacto-yeast extract, 2 g of MgSO4 7H$_2$O, and approximately 6 mL of 1N NaOH was diluted with 1 L of distilled water (pH 7.5) and sterilized with an autoclave) then centrifuged and then it was suspended in 20 mL of 10 mM MgSO$_4$ solution.

(2) 100 mL of this E-coli suspension solution and 100 mL of phage dilution (the amount in which 25,000 plaque are created on the plate for screening (9 cm×13 cm)) were mixed and left for 20 minutes at 37° C., then it was mixed with 8 mL of 50° C. 0.7% top agar (0.7 g of agarose was added per 100 mL) and sown on the plate for screening (9 cm×13 cm). The plate was left at 37° C. and then it was cultured until the size of the plaque reached 0.5 mm.

(3) A nylon membrane, HYBOND-N (Amersham Corp.) was cut to the size of the plate and then placed on top of topagarose for 30 seconds. This was placed on a filter dipped with a denaturation solution (0.5 M NaOH, 1.5 M NaCl) with the side that came in contact with the plaque up. A second membrane was placed on the topagarose, and left for one minute. Similarly, it was placed on the filter dipped in the denaturation solution. After it was left for 5 minutes, the second membrane was moved onto a filter dipped with a neutralization solution (0.5M Tris-HCl, pH 8.0, 1.5M NaCl). After it was left for 5 minutes, it was well washed twice with 2×SSPE (0.02M, NaH$_2$PO$_4$ pH 7.4, 0.3M NaCl, 2 mM EDTA) and then dried.

(4) In order to use the whole length of the cDNA of the isolated naat-A in advance as a probe, those that were at the site of the HindIII of the plasmid vector pYH23 and the NotI sites were cut out and purified. These were labeled with [α-$^{32}$P] dATP using a RANDOM PRIMER DNA LABELING KIT VER. 2 (Takara Shuzo Co., Ltd.)).

Prehybridization was carried out for 1 hour at 65° C. with 30 mL of hybridization buffer (6×SSPE, 5×Denhart solution, 0.1% SDS, 100 mg/mL altered salmon spermary DNA) that was preheated to 65° C., and the hybridization buffer was replaced (25 mL).

The probe prepared as described above was added to this, and hybridization was carried out for 12 hours at 65° C. The membrane was cleaned with a cleaner (5×SSPE) heated to 65° C. in advance twice for 10 minutes, and once with a highly stringent cleaner (2×SSPE, 0.1% SDS) at 65° C. The membrane was wrapped with Saran Wrap, and photosensitized overnight to an imaging plate (Fuji Photo Film Co., Ltd.) and results were obtained with an imaging analyzer (Fuji Photo Film Co., Ltd.).

The reagent used is such that 20×SSPE (0.2 M NaH$_2$PO$_4$ pH 7.4, 3 M NaCl and 20 mM EDTA), 50× denhart solution, 5 g of Ficoll 400, 5 g of polyvinylpyrrolidone (MW 360,000) and 5 g of calf serum albumin were dissolved in 500 mL of distilled water and filtered with a 0.45 mm filter.

(5) What emerged on both of the two membranes was determined to be positive and the plaque that corresponded to the location was cut out from the petridish. That which was cut out was placed in an SM solution (50 mM Tris-HCl pH7.5, 0.1M NaCl, 7 mM MgSO$_4$, and 0.01% gelatin) and stored at 4° C. Then, using this phage solution, a second and third screening was carried out in a similar manner. In the end 5 phages were obtained.

The phage DNA of each of the five phages obtained as described above was isolated and a restriction map was created. It was found that the same fragments were increased for all the cases. Namely it was found that all of the obtained 5 phages were derived from the same part of the genome. In addition, it was assumed that the naat used for the probe was contained. Therefore the base sequence was determined for one of these. (See FIG. 7.) In FIG. 7, E is EcoRI, H is HindIII, B is BamHI and N is NotI. The NotI site at both sites is the NotI on the arm of λFIXII.

Example 6

Figure 8:
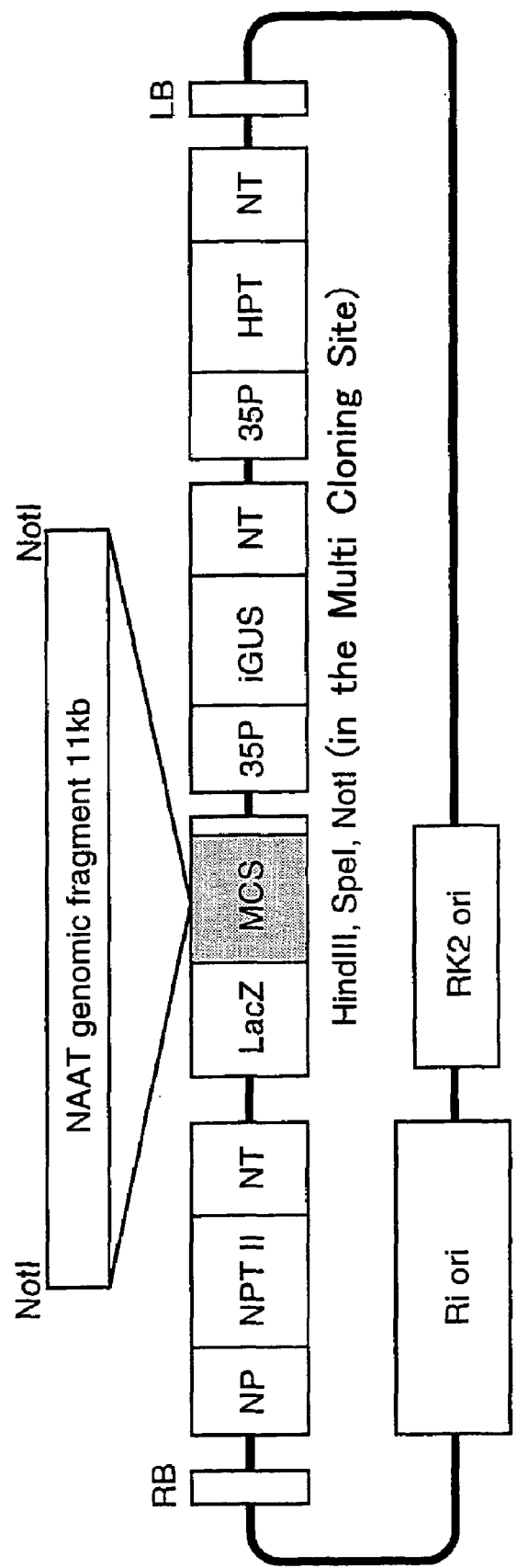
FIG. 8 shows the genetic sequence of the binary vector pBIGRZ1 for a transformed gramineae in which a fragment of the NAAT genome is inserted.

Sub-Cloning and Determination of the Base Sequence (1) The phage DNA shown in FIG. 7 is inserted in the NotI site of the plasmid vector-pBIGRZ1 in which the 10 kb or more fragments can be inserted and a transformation of the gramineae using agro-bacterium can be carried out. (See FIG. 8.) 11.0 kbp of fragments, from the first NotI site to the NotI site located at 11.0 kb of the phage DNA shown in FIG. 7 was cut out and inserted at the NotI site of the pBIGRZ1. (See FIG. 8.) In FIG. 8, NPTII is a kanamycin resistant gene, HPT is a hygromycin resistant gene, GUS is a β glucuronidase gene with intron, LacZ is a β galactosidase gene, 35P is a 35S promoter, NP is an NOS promoter, NT is an NOS terminator, MCS is a multi-cloning site, and Riori is an Ri plasmid replication starting point.

In other words, the base sequence was determined for this 11.0 kb. For the transforming of the rest of the gramineae, this created construct was used.

(2) pBIGRZ1 is stably maintained in the *E. coli* (XL1-BLUE). *E-coli* having this construct were cultured and the plasmid was extracted from here using plasmid adjuster PI-50α. (Kurashiki Boseki Co., Ltd.)

(3) The fragments up to 11.0 kb that are shown in FIG. 7 are classified into 4 sections of A to D and these were introduced to the EcoRI site (B. C) of the plasmid vector of pBluescript SK (−) or the NotI and EcoRI site (A, D).

(4) The base sequence from both sides of the fragments for the fragments A to D was determined by the primer (M13 forward primer, M13 reverse primer) based on the sequence on the plasmid. The DNA sequencer DSQ-2000L from Shimadzu, Ltd. was used to determine the base sequence.

(5) The primer to read further from the portion of the base sequence was determined for each fragment and created, and the primer to confirm the already-read sequence in reverse was created and the base sequences were determined in series. At the end, the sequence was determined for all the fragments in both directions from 5' and 3'. The sequence of the primers used to determine the base sequence of each fragment is shown as follows.

These primers are labeled with the fluorescein isothiocyanate, FITC, at the 5' edge in order to be used by the DSQ-2000L.

Primers for Fragment A
 Name: Sequence F-A1F: FITC-5'-gct act agt agt att cct ggt gta g (SEQ. ID No. 4)
 Name: Sequence F-A1R: FITC-5'-gga gta cta cta gac tac acc agg a (SEQ. ID No. 5)
 Name: Sequence F-A2F: FITC-5'-aca tgc gca tgc atg aat tgc cg (SEQ. ID No. 6)
 Name: Sequence F-A2R: FITC-5'-caa ttc atg cat gcg cat gtg cc (SEQ. ID No. 7)

Primers for Fragment B
 Name: Sequence F-B1F: FITC-5'-ggt caa gta tgc agt atg ttg gaa c (SEQ. ID No. 8)
 Name: Sequence F-B1R: FITC-5'-gtt cca aca tac tgc ata ctt gac c (SEQ. ID No. 9)
 Name: Sequence F-B2F: FITC-5'-cta gaa gcc tat gga tgt ttc ttt tgg (SEQ. ID No. 10)
 Name: Sequence F-B2R: FITC-5'-cca aaa gaa aca tcc ata ggc ttc tag (SEQ. ID No. 11)
 Name: Sequence F-B3F: FITC-5'-agt tct tat caa ttt ccg aga tga c (SEQ. ID No. 12)
 Name: Sequence F-B3R: FITC-5'-ata gtc atc tcg gaa att gat aag a (SEQ. ID No. 13)
 Name: Sequence F-B4F: FITC-5'-agt ggt cac cat gcg gac caa cac c (SEQ. ID No. 14)
 Name: Sequence F-B4R: FITC-5'-ggt gtt ggt ccg cat ggt gac cac t (SEQ. ID No. 15)

Primers for Fragment C
 Name: Sequence F-C1F: FITC-5'-cac cgg cca gtt caa ctg cta cgc (SEQ. ID No. 16)
 Name: Sequence F-C1R: FITC-5'-gcg tag cag ttg aac tgg ccg gtg (SEQ. ID No. 17)
 Name: Sequence F-C2F: FITC-5'-ttt gga gga gat cca tga cga cat a (SEQ. ID No. 18)
 Name: Sequence F-C2R: FITC-5'-tat gtc gtc atg gat ctc ctc caa a (SEQ. ID No. 19)
 Name: Sequence F-C3F: FITC-5'-tct tct cat atg cta ctg tgg gga t (SEQ. ID No. 20)
 Name: Sequence F-C3R: FITC-5'-tga cat gca aca cag gga cat gag c (SEQ. ID No. 21)

Primers for Fragment D
 Name: Sequence F-D1F: FITC-5'-cat gct gac gaa gag cga ggt cat a (SEQ. ID No. 22)
 Name: Sequence F-D1R: FITC-5'-ccc agg ata tga cct tag tgg ttg g (SEQ. ID No. 23)

(6) For the portion of the sequence that could not be determined completely, the following primers were newly synthesized by using the ABI PRISM™ 310 genetic analyzer that is an automatic DNA sequencer from PerkinElmer Japan, Inc.

Primers for Fragment B
 Name: Sequence B5F: 5'-gaa tgg caa act ggg tcc gca tta c (SEQ. ID No. 24)
 Name: Sequence B5R: 5'-gta atg cgg acc cag ttt gcc att c (SEQ. ID No. 25)
 Name: Sequence B6F: 5'-ctg gtt gtt gtg gcc tgg acg aaa c (SEQ. ID No. 26)
 Name: Sequence B6R: 5'-gtt tcg tcc agg cca caa caa cca g (SEQ. ID No. 27)
 Name: Sequence B7F: 5'-agc aca aac cct acc tat gtt agg c (SEQ. ID No. 28)
 Name: Sequence B7R: 5'-gcc taa cat agg tag ggt ttg tgc t (SEQ. ID No. 29)

Primers for Fragment C
 Name: Sequence C4F: 5'-tgg aat ttc gcc cgg ggc aag gac (SEQ. ID No. 30)
 Name: Sequence C4R: 5'-ccc tgt gac aag tgc tct gct acg (SEQ. ID No. 31)
 Name: Sequence C5F: 5'-tct ggg atc tca gtg cat cca aca (SEQ. ID No. 32)
 Name: Sequence C5R: 5'-gaa gca tat atc agt caa aca taa cc (SEQ. ID No. 33)—.

In addition, in order to determine the junction of the fragments A and B and fragments B and C, the following primers were created. The base sequence was determined for the construct created in (1) using the ParkinElmer Japan, Inc. automatic DNA sequencer ABI PRISM™ 310 genetic analyzer.

Border Between Fragments A and B

Name: Sequence A-eF: 5'-cac atc ctt tgc ctt gct gaa tat gg (SEQ. ID No. 34)

Name: Sequence B-tR: 5'-cag tag tac taa tta atc acc tta gta gc (SEQ. ID No. 35)

Border Between Fragments B and C

Name: Sequence B-eF: 5'-cac gat caa cca aag aat gtc ctc c (SEQ. ID No. 36)

Name: Sequence C-tR: 5'-tac ttg tat atg cag ctc cag cac (SEQ. ID No. 37)

(7) The sequence identification number 3 in the sequence listing of the determined 10,966 bp base sequence is shown. The entire sequence is shown in FIGS. 9A through 9D (without base numbers).

From the obtained base sequence, it was found that this 10,966 bp gene is a fragment of the barley genome that codes the naat-A and naat-B obtained so far. The order was naat-B and naat-A.

At the 109th location, 5' upstream, exon, intron, and 3' downstream of naat-A and naat-B were determined by comparing with the cDNA as shown. In the 10th location, uppercase letters represent the exon portion transplanted to cDNA and lowercase letters represent the rest. The base numbers for the exon portion are as follows.

naat-B
  First exon 579–1299 (Starting codon 6518)
  Second exon 1483–1825
  Third exon 1922–2140
  Fourth exon 2244–2303
  Fifth exon 2761–2916
  Sixth exon 3263–3356
  Seventh exon 3735–4033 (Ending codon 3868)

naat-A
  First exon 6457–6897 (Starting codon 6518)
  Second exon 7029–7371
  Third exon 7479–7697
  Fourth 4 exon 7784–7843
  Fifth exon 8285–8440
  Sixth exon 8738–8831
  Seventh exon 9414–9732 (Ending codon 9547)

This schematic view is shown in FIG. 11. The exon portion is shown as the shaded portion. Both genes are formed with 6 introns and 7 exons. In addition, the location of the insertion of the intron was homological. FIG. 12 shows where in the cDNA, and which size of intron was inserted. FIGS. 13 and 14 show the amino acid sequence of naat-A and naat-B estimated from the cDNA.

Example 7

Transforming Method of Gramineae Introduced with a Barley Genome Naat

The transformation method of the gramineae introduced with the genome naat of barley obtained in Example 6 described above was carried out in a similar manner to the 35S transformed gramineae except at those points shown in (1) to (3) as follows.

(1) The callus induction was carried out at 28° C. in a dark place, and the callus induction medium comprised 0.3 g/L of N6 inorganic salt and N6 vitamin, 30 g/L of casamino acid, 2 mg/L of sucrose, 2.8 g/L of 2, 4-D, 4 g/L of proline and gelrite (pH5.8).

(2) It was infected with agro-bacterium at 25° C. and a coexisting culture medium comprising 30 g/L of N6 inorganic salt and N6 vitamin, 10 g/L of sucrose, 1 g/L of glucose, 2 mg/L of casamino acid, 20 mg/L of 2, 4-D, 2 g/L of acetosyringone and gelrite (pH5.2). It was carried out with a placement of the filter.

(3) For the selection, a selection medium was used containing 10 mg/L for the first week, 30 μg/L for the next week and 50 mg/L for the last two weeks of hygromycin, and it was cultured at 28° C. in a dark place.

The selection medium comprising 1 g/L of N6 inorganic salt and N6 vitamin, casamino acid, 30 g/L of sucrose, 2 mg/L of 2, 4-D, 250 mg/L of Claforan, 10 to 50 mg/L of hygromycin and 2 g/L of gelrite (pH5.8) was used and a redifferentiation medium comprising 30 g/L of MS inorganic salt and MS vitamin, sucrose, 30 g/L of sorbitol, 2 g/L of casamino acid, 1.1 g/L of MES, 2 mg/L of NAA, 1 mg/L of kinetin, 250 mg/L of Claforan (Hoechst Marion Roussel Ltd. Japan), 50 mg/L of hygromycin, and 4 g/L of gelrite (pH5.8) was used and it was cultured at 28° C.

Example 8

The Inspection of the Iron Deficiency Resistance of Gramineae with a Genome Naat Introduced The inspection of the iron deficiency resistance of gramineae with a genome naat introduced was carried out for 39 individuals out of the obtained regenerators (T1) and 15 controls in which only the vector was introduced in a similar manner to the 35S transformed plant. From the 5th week after the transplant, the height of the plants was measured every week or every other week. They were transferred twice every 4 to 5 weeks to a pot with an increased soil size.

The leaves of the transformed gramineae with a genome naat turned yellow by the second week after they were transplanted to an alkaline soil, however, on the 4th to 5th week, the new leaves started to become a dark green and recover, and then started to show vigorous growth. Compared to this, the control group in which only the vector was introduced continued to have yellow leaves for a long period of time, and from approximately the 8th week, new leaves started to turn green. From this fact, it was found that the introduction of naat allows the gramineae to have an iron deficiency resistance. (See FIGS. 15 and 16.)

FIG. 15 is a photo that shows the growth state of the $10^{th}$ week after being transplanted to an alkaline soil.

FIG. 15 shows the control gramineae in which only the vector was transplanted. The gramineae on the right was transformed with a genome naat.

The transition of the height of the plants after being transplanted to an alkaline soil is shown in FIG. 16. In FIG. 16, the Y axis shows the height of the plant (cm) and the X axis shows the number of days after it was transplanted to the alkaline soil. In FIG. 16, the one on the left is the gramineae transformed with a genome naat and the one on the right is the control gramineae in which only the vector was transplanted.

Through this, it was found that the introduction of a genome naat allows an increase in the iron deficiency resistance for a gramineae.

INDUSTRIAL APPLICABILITY

The present invention provides a new gramineae with iron deficiency resistance and provides a new gramineae that can be grown in a cultivation area with an iron deficiency.

In addition, the present invention provides the new knowledge that a gramineae with improved iron absorbency can be obtained by introducing a gene that codes the enzyme along the mugineic acid biosynthesizing route, to a gramineae.

The invention claimed is:

1. A method for producing a transgenic gramineae plant having iron deficiency resistance, comprising transforming a gramineae plant with an isolated polynucleotide comprising the base sequence of SEQ ID NO. 3.

2. The method according to claim 1, wherein the polynucleotide further comprises a promoter.

3. The method according to claim 1, wherein the polynucleotide encodes a barley nicotianamine aminotransferase (NAAT).

4. A transgenic gramineae plant comprising an isolated polynucleotide comprising the base sequence of SEQ ID NO. 3, wherein said transgenic gramineae plant has resistance to iron deficiency.

5. A transgenic seed of the transgenic gramineae plant according to claim 4.

6. A transgenic cell of the transgenic gramineae plant according to claim 4.

7. A method of growing a gramineae plant in an iron deficient field comprising planting the transgenic gramineae plant of claim 4, in said field under conditions to promote growth of said transgenic gramineae plant.

8. The transgenic gramineae plant according to claim 4, wherein the polynucleotide encodes a barley nicotianamine aminotransferase (NAAT).

9. A method of growing a gramineae plant in an iron deficient field comprising planting the transgenic seed of claim 5 in said field under conditions to promote growth of a transgenic plant.

* * * * *

SEQUENCE LISTING

<160> NUMBER OF SEQ ID NOS: 37

<210> SEQ ID NO 1
<211> LENGTH: 461
<212> TYPE: PRT
<213> ORGANISM: naat A

<400> SEQUENCE: 1

Met Val His Gln Ser Asn Gly His Gly Glu Ala Ala Ala Ala Ala Ala
1               5                   10                  15

Asn Gly Lys Ser Asn Gly His Ala Ala Ala Asn Gly Lys Ser Asn
            20                  25                  30

Gly His Ala Ala Ala Ala Val Glu Trp Asn Phe Ala Arg Gly Lys
        35                  40                  45

Asp Gly Ile Leu Ala Thr Thr Gly Ala Lys Asn Ser Ile Arg Ala Ile
        50                  55                  60

Arg Tyr Lys Ile Ser Ala Ser Val Glu Glu Ser Gly Pro Arg Pro Val
65                  70                  75                  80

Leu Pro Leu Ala His Gly Asp Pro Ser Val Phe Pro Ala Phe Arg Thr
                85                  90                  95

Ala Val Glu Ala Glu Asp Ala Val Ala Ala Leu Arg Thr Gly Gln
            100                 105                 110

Phe Asn Cys Tyr Ala Ala Gly Val Gly Leu Pro Ala Ala Arg Ser Ala
            115                 120                 125

Val Ala Glu His Leu Ser Gln Gly Val Pro Tyr Lys Leu Ser Ala Asp
    130                 135                 140

Asp Val Phe Leu Thr Ala Gly Gly Thr Gln Ala Ile Glu Val Ile Ile
145                 150                 155                 160

Pro Val Leu Ala Gln Thr Ala Gly Ala Asn Ile Leu Leu Pro Arg Pro
                165                 170                 175

Gly Tyr Pro Asn Tyr Glu Ala Arg Ala Ala Phe Asn Lys Leu Glu Val
                180                 185                 190

Arg His Phe Asp Leu Ile Pro Asp Lys Gly Trp Glu Ile Asp Ile Asp
            195                 200                 205

Ser Leu Glu Ser Ile Ala Asp Lys Asn Thr Thr Ala Met Val Ile Ile
    210                 215                 220

Asn Pro Asn Asn Pro Cys Gly Ser Val Tyr Ser Tyr Asp His Leu Ala
225                 230                 235                 240

Lys Val Ala Glu Val Ala Arg Lys Leu Gly Ile Leu Val Ile Ala Asp
                245                 250                 255

Glu Val Tyr Gly Lys Leu Val Leu Gly Ser Ala Pro Phe Ile Pro Met
                260                 265                 270

Gly Val Phe Gly His Ile Ala Pro Val Leu Ser Ile Gly Ser Leu Ser
            275                 280                 285

Lys Ser Trp Ile Val Pro Gly Trp Arg Leu Gly Trp Val Ala Val Tyr
    290                 295                 300

Asp Pro Thr Lys Ile Leu Glu Lys Thr Lys Ile Ser Thr Ser Ile Thr
305                 310                 315                 320

Asn Tyr Leu Asn Val Ser Thr Asp Pro Ala Thr Phe Val Gln Glu Ala
                325                 330                 335

Leu Pro Lys Ile Leu Glu Asn Thr Lys Ala Asp Phe Phe Lys Arg Ile
                340                 345                 350

Ile Gly Leu Leu Lys Glu Ser Ser Glu Ile Cys Tyr Arg Glu Ile Lys

```
                355                 360                 365
Glu Asn Lys Tyr Ile Thr Cys Pro His Lys Pro Glu Gly Ser Met Phe
    370                 375                 380

Val Met Val Lys Leu Asn Leu His Leu Leu Glu Glu Ile His Asp Asp
385                 390                 395                 400

Ile Asp Phe Cys Cys Lys Leu Ala Lys Glu Glu Ser Val Ile Leu Cys
                405                 410                 415

Pro Gly Ser Val Leu Gly Met Glu Asn Trp Val Arg Ile Thr Phe Ala
                420                 425                 430

Cys Val Pro Ser Ser Leu Gln Asp Gly Leu Glu Arg Val Lys Ser Phe
                435                 440                 445

Cys Gln Arg Asn Lys Lys Lys Asn Ser Ile Asn Gly Cys
    450                 455                 460

<210> SEQ ID NO 2
<211> LENGTH: 551
<212> TYPE: PRT
<213> ORGANISM: naat B

<400> SEQUENCE: 2

Met Ala Thr Val Arg Gln Ser Asp Gly Val Ala Ala Asn Gly Leu Ala
1               5                   10                  15

Val Ala Ala Ala Asn Gly Lys Ser Asn Gly His Gly Val Ala Ala
            20                  25                  30

Ala Val Asn Gly Lys Ser Asn Gly His Gly Val Asp Ala Asp Ala Asn
            35                  40                  45

Gly Lys Ser Asn Gly His Gly Val Ala Ala Asp Ala Asn Gly Lys Ser
    50                  55                  60

Asn Gly His Ala Glu Ala Thr Ala Asn Gly His Gly Glu Ala Thr Ala
65                  70                  75                  80

Asn Gly Lys Thr Asn Gly His Arg Glu Ser Asn Gly His Ala Glu Ala
                85                  90                  95

Ala Asp Ala Asn Gly Glu Ser Asn Glu His Ala Glu Asp Ser Ala Ala
            100                 105                 110

Asn Gly Glu Ser Asn Gly His Ala Ala Ala Ala Glu Glu Glu Glu
        115                 120                 125

Ala Val Glu Trp Asn Phe Ala Gly Ala Lys Asp Gly Val Leu Ala Ala
        130                 135                 140

Thr Gly Ala Asn Met Ser Ile Arg Ala Ile Arg Tyr Lys Ile Ser Ala
145                 150                 155                 160

Ser Val Gln Glu Lys Gly Pro Arg Pro Val Leu Pro Leu Ala His Gly
                165                 170                 175

Asp Pro Ser Val Phe Pro Ala Phe Arg Thr Ala Val Glu Ala Glu Asp
                180                 185                 190

Ala Val Ala Ala Val Arg Thr Gly Gln Phe Asn Cys Tyr Pro Ala
        195                 200                 205

Gly Val Gly Leu Pro Ala Ala Arg Ser Ala Val Ala Glu His Leu Ser
    210                 215                 220

Gln Gly Val Pro Tyr Met Leu Ser Ala Asp Asp Val Phe Leu Thr Ala
225                 230                 235                 240

Gly Gly Thr Gln Ala Ile Glu Val Ile Ile Pro Val Leu Ala Gln Thr
                245                 250                 255

Ala Gly Ala Asn Ile Leu Leu Pro Arg Pro Gly Tyr Pro Asn Tyr Glu
            260                 265                 270
```

-continued

```
Ala Arg Ala Ala Phe Asn Arg Leu Glu Val Arg His Phe Asp Leu Ile
            275                 280                 285
Pro Asp Lys Gly Trp Glu Ile Asp Ile Asp Ser Leu Glu Ser Ile Ala
            290                 295                 300
Asp Lys Asn Thr Thr Ala Met Val Ile Ile Asn Pro Asn Asn Pro Cys
305                 310                 315                 320
Gly Ser Val Tyr Ser Tyr Asp His Leu Ser Lys Val Ala Glu Val Ala
                325                 330                 335
Lys Arg Leu Gly Ile Leu Val Ile Ala Asp Glu Val Tyr Gly Lys Leu
            340                 345                 350
Val Leu Gly Ser Ala Pro Phe Ile Pro Met Gly Val Phe Gly His Ile
            355                 360                 365
Thr Pro Val Leu Ser Ile Gly Ser Leu Ser Lys Ser Trp Ile Val Pro
            370                 375                 380
Gly Trp Arg Leu Gly Trp Val Ala Val Tyr Asp Pro Arg Lys Ile Leu
385                 390                 395                 400
Gln Glu Thr Lys Ile Ser Thr Ser Ile Thr Asn Tyr Leu Asn Val Ser
            405                 410                 415
Thr Asp Pro Ala Thr Phe Ile Gln Ala Ala Leu Pro Gln Ile Leu Glu
            420                 425                 430
Asn Thr Lys Glu Asp Phe Phe Lys Ala Ile Ile Gly Leu Leu Lys Glu
            435                 440                 445
Ser Ser Glu Ile Cys Tyr Lys Gln Ile Lys Glu Asn Lys Tyr Ile Thr
            450                 455                 460
Cys Pro His Lys Pro Glu Gly Ser Met Phe Val Met Val Lys Leu Asn
465                 470                 475                 480
Leu His Leu Leu Glu Glu Ile Asp Asp Ile Asp Phe Cys Cys Lys
            485                 490                 495
Leu Ala Lys Glu Glu Ser Val Ile Leu Cys Pro Gly Ser Val Leu Gly
            500                 505                 510
Met Ala Asn Trp Val Arg Ile Thr Phe Ala Cys Val Pro Ser Ser Leu
            515                 520                 525
Gln Asp Gly Leu Gly Arg Ile Lys Ser Phe Cys Gln Arg Asn Lys Lys
            530                 535                 540
Arg Asn Ser Ser Asp Asp Cys
545                 550
```

<210> SEQ ID NO 3
<211> LENGTH: 10966
<212> TYPE: DNA
<213> ORGANISM: Horudeum vulgare L. var. Igri

<400> SEQUENCE: 3

```
ctcgatccca ttgcaatggt atgattagct atcaaacgaa agaaagagat ggcatgtgcc    60
ctgtgtgtca tccctcactg gcttggcgaa tggcgatacc gagttaggta gagtgttttt   120
ttagcatgat gtctgccggc actgccaaga aaactgcgtg cagcggactg caggagagtt   180
gagcgatgca tgctttgtga tgagcggagc tgagtgggtg tcactaactg aacccaatca   240
gcattgggtg agtcgagtcg agaagcatca tgcttcctgc gtcccgatcc gcttatcttt   300
ttctcccaaa ttattaaaga gggatagatg atggtgtgct gggttgggta gagtacgtgc   360
atagaaccaa agcgaggcgc cgaaaatatg ccggggataa tggtggcagg ccgcaacggc   420
cacgcccgtc agctggcagc ggcgtgccag agcgtgccag agcgtgcgcg cgtgcgtgct   480
tcttgctgcc ggccccggtt cgtgtgcggt cagagcaacg gctatatagg accgtcaatc   540
```

```
accgctactc aatccgtccc caactcgttt cctattaccg ctactagtag tattcctggt    600
gtagtctagt agtactcctc ctcctccttc tcctcctacc cgtttcctca tggccaccgt    660
acgccagagc gacggagtcg ccgcgaacgg ccttgccgtg ccgcagccg cgaacggcaa     720
gagcaacggc catggcgtgg ctgccgccgt gaacggcaag agcaacggcc atggcgtgga    780
tgccgacgcg aacggcaaga gcaacggcca tggcgtggct gccgacgcga acggcaagag    840
caacggccat gccgaggcca ctgcgaacgg ccacggcgag gccactgcga acggcaagac    900
caacggccac cgcgagagca acggccatgc tgaggccgcc gacgcgaacg gcagagcaa     960
cgagcatgcc gaggactccg cggcgaacgg cgagagcaac gggcatgcgg cggcggcggc   1020
agaggaggag gaggcggtgg agtggaattt cgcgggtgcc aaggacggcg tgctggcggc   1080
gacgggggcg aacatgagca tccgggcgat acggtacaag atcagcgcga gcgtgcagga   1140
gaaggggccg cggcccgtgc tgccgctggc ccacggggac ccgtccgtgt tcccggcctt   1200
ccgcacggcc gtcgaggccg aggacgccgt cgccgccgcg ctgcgcaccg ccagttcaa    1260
ctgctacccc gccggcgtcg gcctccccgc cgcacgaagg taacaacaac aacaacacaa   1320
gaacaatttc cttttcgcgt gtcgtgtcgc gcggcaatcc atgcatgcgc atgtgccgct   1380
ttcacgtgtc cgtccgtccg tccaccgttc cttcctcctc cctacgccca tgagaaatct   1440
gaccttctcc caccttatac caaacaaaac aaaaaaacac agcgccgtgg cagagcacct   1500
gtcgcagggc gtgccgtaca tgctatcggc cgacgacgtc ttcctcaccg ccggcgggac   1560
ccaggcgatc gaggtcataa tcccggtgct ggccagacc gccggcgcca acattctgct    1620
ccccaggcca ggctacccaa actacgaggc gcgcgccgcg ttcaacaggc tggaggtccg   1680
gcatttcgac ctcatccccg acaaggggtg ggagatcgac atcgactcgc tggaatccat   1740
cgccgacaag aacaccaccg ccatggtcat cataaaccc aacaaccgt gcggcagcgt     1800
ttactcctac gaccatctgt ccaaggtttc acatcctttg ccttgctgaa tatggattca   1860
gttcagtgca cctgctgaat tcttttttgcc aatcgcatac tgactgatgt tgctcaatta  1920
ggtcgcggag gtggcgaaaa ggctcggaat attggtgatt gctgacgagg tatacggcaa   1980
gctggttctg ggcagcgccc cgttcatccc aatgggagtg tttgggcaca tcaccctgt    2040
gctgtccata gggtctctgt ccaagtcatg gatagtgcct ggatggcggc ttggatgggt   2100
agcggtgtac gaccccagaa agatcttaca ggaaactaag gtacttaaat ctctatatca   2160
ttcttttcaa atgctactaa ggtgattaat tagtactact gtacaatata tttgctaaat   2220
ttgtactgac attttttgtgg tagatctcta catcaattac gaattacctc aatgtctcga   2280
cagacccagc aaccttcatt caggtcagtc tttggtattt acctcgtttc aagaaataaa   2340
gtctttggta tttactcctc cttgtcctat tttgctccgg tccctatgtt gtaggcagcc   2400
cacgtgcatg tcaagtgacc gttttttcac attaagtttg aaagtcaaag tcagacacat   2460
acacttgtag ttatttttacc tttgtttgct ttgatccgat aaaataaaaa aatacaaaaa   2520
ctgaacctac tgttgaatat aaccactgtt cttacaagat atacatgatt gcactatggg   2580
catgccatat tcttttgggt caagtatgca gtatgttgga acctctttta gaaaatagat   2640
acattgtact atgagtatac catttttatta agaatttcat attttgatat ccttgatggt   2700
attgttctct tgtgattcac acgatttact tgtggttttt tgtactatca aattgttcag   2760
gcagctcttc ctcagattct tgagaacaca aggaagatt tctttaaggc gattattggt    2820
ctgctaaagg aatcatcaga gatatgctac aaacaaataa aggaaaacaa atacattaca   2880
```

```
tgtcctcaca agccagaagg atcaatgttt gtcatggtaa gcctattttg tgaagtaaaa    2940
aaatcttagg gagtgtcagt aatcataaac ttatttatat aggattaatc tgggaccgaa    3000
atgcatccaa cataattact tcaaattcaa attcaaatta cattcttccg tacatatttt    3060
tgaagatgca tgtattttaa gaataatgac gagagctaaa gttatgctac gactaatcat    3120
ctggatatcc tttgtccatc ttttgttat actgtggaat gttaatgtc aaatcatatt      3180 acacaaatat ccatgctagt ttctagaaag attgattatt tttctgtaac catgaactcc    3240
gtattaactt ccatgtaaac aggtgaaact gaacttacat cttttggagg aaatagacga    3300
tgacattgat ttttgctgca agctcgcaaa agaagaatca gtaatcttat gcccaggtag    3360
gaatccattg ttgattttg actgtatatg aagttcttat caatttccga gatgactata     3420
catataaatg attaccatat tatggtcaga aattgtataa cagtgttaga atattctgtg    3480 aagactttt taacacaata ttctgtgaag actagatatc atgtacttct ccttgttttc     3540
ttgacctgat gtccttcgtc acatgttgtg ctcctcacaa aaaatagca agcacatgtt     3600 tcaaataatt gttaataata taatttagcc tttaatttat atggttctat tttgagatat    3660
ttttgtagtc caacttatat atttgtgact attctcaaaa acaaaactta tatatgtgtg    3720
cctctcaaat gtagggagtg ttcttggaat ggcaaactgg gtccgcatta cttttgcttg    3780
tgttccatct tctcttcaag atggtctcgg aaggatcaaa tcattctgtc aaaggaacaa    3840
gaagagaaat tcgagcgatg attgctagtt gtatatctga ctgaagctgt aaatcattcc    3900
cagtatcccc atctatatct ttcaataaaa tggaactttt agttctctat gaatagaagt    3960
caacatctcc ttgaatatgt tctggttgtt gtggcctgga cgaaacatag tgaatgttat    4020
gttagtgaag ttacattggc gtcgaagatc tttgaagttt ttttttttt ttgggggggg     4080 gggggggggg tgctttgata ttactcttaa gtacacgttc tctcaagtta tgtcaaagca    4140
ctttgtaaac aattgtagat ttggtatcat gatatggatt aaactagtca gatacttggt    4200
aagcacaaac cctacctatg ttaggctcac taaggtggcg tttggttcga gagagaggaa    4260
ggatcagttg atgatatccc caatcatcga agtaaatcat gtgttgttgc taccactttt    4320
ctacaatcct agtagctgca tgcgttgagc tactgatcaa caccactgca caaccatatt    4380
ctctgtgcaa aatcggcacc caaagattac atctcacagc tgaagcaacc accaaatttg    4440
aagagaggaa ccctcacaaa gacctttgag tgccccccac aatgcatggt taggccgccg    4500
tcgcaggccg gagtggtcac catgcggacc aacaccaact ccaacggggg agcacgtcac    4560
cgattactga aattccccaa acaattctta atttgtgaac aaaatttaaa aacaggaaca    4620
atttttgaat ttgtgaacaa attttttaaa cgggtattcc tgaacatttt tcaaaattgt    4680
gatcaaaatt ttaaaacgac ttcttctca aatttgagca atatttaaaa ttataaaaaa     4740
gttcaacaat tttgaacttt ttaaaaatta gcgagaacat tttgaaattc taaatatttt    4800
cgaatttgga acattttttc tatttctgaa caaaaattga aaatacgaac gtaatttgga    4860 ataaatttg gaaatgcga ttttttgaaa tttctgaaca tattttgaaa aacaaaaaaa      4920
ctttaaaagg taaataaaa ataaaataaa aatagaaaca taaaaataag caaaaaata      4980 aaagaaatcc gagaaaagcc aactgggaat agcacatgga aaacccagc cgtccgccgc     5040 actgtgtaaa gctataagtg agccggccca agcctcgtcg tctcatcata ccctgtgcga    5100
aaccccgaca attcgttgca ctatgcggcg aataggcttt tccaggagct cctgtcttcc    5160
ggttatgggt catttgcaca cccctcctcc acttgggcca ggctattata cttttttcc     5220 ttctttcgac ctcacgttac tacgccagtt tagtttttgg aagcgaccaa ccggttttgt    5280
```

```
gaaggttcta gaaactcaac cattttgggg aagcttctag aagcctatga atgtttcttt      5340
tggacatgta ttatttgtgt ttttctttt tcaaattgca caatctttt tcaaattcat       5400 gattttgtg aaacttgtga ttttttgaat ccgtgatttt ttttcctaaa tccgtgtttt      5460
gaaaaaaact gtggactttt ccgaaattaa tgaacatttg tttgcaagat cgatgatcct     5520
tttcaaatga gcgatttttt tctaaaatat ccacatattt ttcatattca taagctttcc     5580
ttttaatcgt gaactatctt agcatttggt gaactttat taatttctt tataaaatga       5640 ttttttttca aaagccaacg gttaacggtt gaccgctgaa ccacaaccac aaaccgggga     5700
aaccattgac tcgctgaaca gggcagggct ttcatatgat tgggtggtct aataccagcg     5760
cccctgacta ctaaacgaag gaattgcaaa ttttaccaac cactactatg gtaaaaaatg     5820
aatatcacga taaaaaggg gaaaaaaaac tatacccctga aaatccctct gtttctaaat     5880
atttgttgtt ggggagaact aatctgaaag aactaatcta gttctccgca ataacaaata    5940
ttatgattcg gggggagtat aactattaca cgatcaacca agaatgtcc tccaagaaaa     6000 acccaaagaa agtgctagag ttttgttttc aaggaccgaa agatagagat agcattctga    6060
attaggtcca tctttttccc aaggattgaa agaaagagat agaattctga attaggtgcg    6120
gagatatcat ttctggatta ggtacaattg ttttgccggc acagccaaac ccgcagtgg     6180 agccggaatt ggaattgagt gggtggagtc gagaagcatg gttcatgcgt tctcaaagag    6240
tgtagccagt agtgtgtgct ccttggtgct ggagctgcat atacaagtac ataaaacaaa    6300
gacgatcagc tggcagcgtg cctgcatgcg tgcttcttgc tgccgccccg gaagcccgg     6360 ttgatgtgcg caggcgagtg gcgacgggac cgacggctat aaagcacggc caagcaccgc    6420
cgccgttctc aatccatcca tcccttagct gatttgattg actagctagt tcattccctg    6480
ccacactgct agtactcctc ctcgtttcct cgtggcaatg gtacaccaga gcaacggcca    6540
cggcgaggcc gccgccgccg ccgccaacgg caagagcaac gggcacgccg ccgccgcgaa    6600
cggcaagagc aacgggcacg cggcggcggc ggcggtggag tggaatttcg cccgggggcaa   6660 ggacggcatc ctggcgacga cggggggcgaa gaacagcatc cggcgatac ggtacaagat    6720 cagcgcgagc gtggaggaga gcgggccgcg gcccgtgctg ccgctggccc acggtgaccc    6780
gtccgtgttc ccgccttcc gcacggccgt cgaggccgag gacgccgtcg ccgccgcgct     6840
gcgcaccggc cagttcaact gctacgccgc cggcgtcggc ctccccgccg cacgaaggta    6900
acatttacag cttcaccgta atgtatgcgt gagcatgcat gcgccggttt acttacgtgc    6960
ccgccgctgt tcttccccgg tgcgttcaaa attttaacct tctataagta ccttataaaa    7020
acaaacagcg ccgtagcaga gcacttgtca cagggcgtgc cctacaagct atcggccgac    7080
gacgtcttcc tcaccgccgg cggaactcag gcgatcgaag tcataatccc ggtgctggcc    7140
cagactgccg gcgccaacat actgcttccc cggccaggct atccaaatta cgaggcgcga    7200
gcggcattca acaagctgga ggtccggcac ttcgacctca tccccgacaa ggggtgggag    7260
atcgacatcg actcgctgga atccatcgcc gacaagaaca ccaccgcgat ggtcatcata    7320
aacccaaaca atccgtgcgg cagcgtttac tcctacgacc atctggccaa ggttttgcat    7380
ccatgcatcc tctgcctcgt tgatcgaccg gtctgtttga acatagtata tggattgcgt    7440
ttgctaatcg tgtgctgatg atgctgtttg gttatcaggt cgcggaggtg gcaaggaagc    7500
tcggaatatt ggtgatcgct gacgaggttt acggcaaact ggttctgggc agcgccccgt    7560
ttatcccgat gggcgtcttt gggcacattg ccccggtctt gtccattgga tctctgtcca    7620
```

-continued

```
agtcgtggat agtgcctgga tggcgacttg gatgggtggc ggtgtacgac cccacaaaga    7680
ttttagagaa aactaaggta gctttagctc cctatcattc ttctcatatg ctactgtggg    7740
gattagtatt tttgctaaat ttgtactgcc tttgtttatt cagatctcta cgtctattac    7800
gaattacctt aatgtctcaa cggacccagc aaccttcgtt caggttagtc tttggttctt    7860
gccctatttt gctcatgtcc ctgtgttgca tgtcaaatga ccggcttcaa gttagtatat    7920 agagttttg ttaagtgtga atgtcgaagt ccaacatgat ggaagaaaga tacatctatt    7980
tttagtcatt cccctttgtt tgtttgattc cataaaataa ataaacacaa agccagaacc    8040
aactattgaa tagaactatt tttcttagaa aatatacatt gtattttgag catgccatat    8100
tcttttcgat caagtatgca atatattaaa acttgcattg tactacgagt ataccatgtt    8160
gttaagaatt tctttaccta caacaccttg tctcgcatct tcatattttg atatccttga    8220
cattattgtt ctcttatgat tcacacaact taattatgga tttttgtgct atcaaattgt    8280
ttaggaagct cttcctaaaa ttcttgagaa cacaaaagca gatttcttta agaggattat    8340
tggtctacta aaggaatcat cagagatatg ttataggaa ataaggaaa acaaatatat    8400 tacgtgtcct cacaagccag aaggatcgat gtttgtaatg gtaagctaag catagactta    8460 cttttttaagg ttaatctggg atctcagtgc atccaacaaa caatcaaatc aaaatataat    8520
tatgttttgc tatggatctt tttgaagatg catgcatttg aagaataatg aagagagttg    8580
aaattatttt aggactaatc ttcctgatat catttgtcca ttttttttgtt attactgtaa    8640 attggtaaca ctcaaatcat attacaaaaa gtttcctccc attttagta agattgactt    8700 cctttctata accatgtatt aacttccatg taaacaggtc aaactaaact tacatctttt    8760
ggaggagatc catgacgaca taaattttg ctgcaagctc gcaaaggaag aatctgtaat    8820
tttatgtcca ggtaggaatg tatatggcca ttttaaagga aaactatatg gaataataat    8880
atcttcttgt tatactaaac aatacttcct ccatcctaaa ataaatgtct tacacttagc    8940 acaatttat actagatcta gtacaaagtt gaaacagtta ttttgggaca gagggagtag    9000
tatatattgt gtgagaacat aaggttatgt ttgactgata tatgcttctt aaatgtgaaa    9060
catgttctct tatgttttt gattgtatac gaagttctta tcagtttccg agatgactac    9120
acataaatga ttaccatatc attgtcagaa aatgtattac cacattagaa tattcttttct    9180 ttttatgcaa agactagcat ggcatgtact tttccttgta cctatgtgtc tttttttttc    9240
tcgttacatg tttgtgcttc tcacaaaaat aataatacca agcacatgtt ccaaatgatt    9300
attaataatt ttgaggtgtt tttcaaccaa cttatatact ttcatagttc taaaaaaacc    9360
gtatatatgg ttaactctaa caaaaactta tatatgtttt ctctctaata cagggagtgt    9420
tcttggaatg gaaaattggg tccgtattac ttttgcctgc gttccatctt ctcttcaaga    9480
tggactcgaa agggtcaaat cattctgtca aaggaacaag aagaagaatt ctataaatgg    9540
ttgttagttg tacacacccc tagttgtaca tctgactgaa gctgtaaatc atttctagtt    9600
atccccattt atatatttca ataaaacata ttgtaatggt tctgttgtag ctgtccaagt    9660
catgtactct acttttgat gtatttggcc tcattgcctt gcatcagttt caataaaaat    9720
ggttgtgtac acaatgatga tgtagaggcg aggtgttttg accaccttttt caacaaaaat    9780 ctatatcttt caacaaatga aaccttgagt tccctttgag tagaagtcaa catactcctt    9840
gaatatgcta tggtttccat ggtctggatg aaacatgatg aatagaagtg aagttatatc    9900
catgtcaaag tttttaatg tttaatttca ttatgagaac tttgatatta cttctagcac    9960
acattctctg aagtaattgt cagtttggta cttgaaggga cctatatttt tcctattggg   10020
```

-continued

```
gggggggggt gaataggcgg tttataacca attgtatatt tgagaatatc ttaatgtgga    10080
attaaactag gtgaatattt tttccaataa agggtgcttt tattgactca caatgtacca    10140
tcaagggata caatcataat gagtacacaa tcgacatcta cataatcagg ttgcatacgg    10200
ccaacacaca cacacgcaca cacacattca cacacacaaa tcatgctgac gaagagcgaa    10260
gtcatacaag atcaaaacta tgcctaggcg gaggaagaat agaaaaacat gaagaaatga    10320 aaaccgtga ctgacaacat actgaccatc gacgacaaac atctgtagac aacacaaaaa     10380
ctgcgagaaa agttctataa aactggcgcc ttcgagaagg aaacgacgtg caagagttgc    10440
catcatcgga tccaaccact aaggtcatat cctgggtttt catcctgaag atcaaatccg    10500
agcaaactcc gagtaatgtc tttattaggg taacgattca aaaaatgcca caatcatgag    10560
ttatgaccaa ttagaccaga cctaggattt ttatccaaag ctcgagacgg gtactctaga    10620
agtaccatcc aattgaagtc atcccacttg cctcaataca aatagttgca tagatgcacg    10680
gtccatatgg cgagtaatgg acatgagcgc gcatgtgtag gttaacgtga cgtgacaaga    10740
gcctgtcgcc accactcgac gaagtgtttg atggggagga agaagtatgg ctccaccaac    10800
atcccaagtt tgaaacattc tagagcccct taccatactc acaaagcgac aattgatgac    10860
tatctgtatc agacgacaaa tccatgtccg tcactcgctc tatcttggtc attgacatac    10920
tacctggcaa aggcggattc aagccccaga cagcctgggg ggccgc                   10966
```

<210> SEQ ID NO 4
<211> LENGTH: 25
<212> TYPE: DNA
<213> ORGANISM: Primer for fragment A

<400> SEQUENCE: 4
gctactagta gtattcctgg tgtag                                          25

<210> SEQ ID NO 5
<211> LENGTH: 25
<212> TYPE: DNA
<213> ORGANISM: Primer for Fragment A

<400> SEQUENCE: 5
ggagtactac tagactacac cagga                                          25

<210> SEQ ID NO 6
<211> LENGTH: 23
<212> TYPE: DNA
<213> ORGANISM: Primer for Fragment A

<400> SEQUENCE: 6
acatgcgcat gcatgaattg ccg                                            23

<210> SEQ ID NO 7
<211> LENGTH: 23
<212> TYPE: DNA
<213> ORGANISM: Primer for Fragment A

<400> SEQUENCE: 7
caattcatgc atgcgcatgt gcc                                            23

<210> SEQ ID NO 8
<211> LENGTH: 25
<212> TYPE: DNA
<213> ORGANISM: Primer for Fragment B

```
-continued

<400> SEQUENCE: 8
ggtcaagtat gcagtatgtt ggaac                                    25

<210> SEQ ID NO 9
<211> LENGTH: 25
<212> TYPE: DNA
<213> ORGANISM: Primer for Fragment B

<400> SEQUENCE: 9
gttccaacat actgcatact tgacc                                    25

<210> SEQ ID NO 10
<211> LENGTH: 27
<212> TYPE: DNA
<213> ORGANISM: Primer for Fragment B

<400> SEQUENCE: 10
ctagaagcct atggatgttt cttttgg                                  27

<210> SEQ ID NO 11
<211> LENGTH: 27
<212> TYPE: DNA
<213> ORGANISM: Primer for Fragment B

<400> SEQUENCE: 11
ccaaaagaaa catccatagg cttctag                                  27

<210> SEQ ID NO 12
<211> LENGTH: 25
<212> TYPE: DNA
<213> ORGANISM: Primer for Fragment B

<400> SEQUENCE: 12
agttcttatc aatttccgag atgac                                    25

<210> SEQ ID NO 13
<211> LENGTH: 25
<212> TYPE: DNA
<213> ORGANISM: Primer for Fragment B

<400> SEQUENCE: 13
atagtcatct cggaaattga taaga                                    25

<210> SEQ ID NO 14
<211> LENGTH: 25
<212> TYPE: DNA
<213> ORGANISM: Primer for Fragment B

<400> SEQUENCE: 14
agtggtcacc atgcggacca acacc                                    25

<210> SEQ ID NO 15
<211> LENGTH: 25
<212> TYPE: DNA
<213> ORGANISM: Primer for Fragment B

<400> SEQUENCE: 15
ggtgttggtc cgcatggtga ccact                                    25

<210> SEQ ID NO 16
<211> LENGTH: 24
<212> TYPE: DNA
<213> ORGANISM: Primer for Fragment C
```

<400> SEQUENCE: 16
caccggccag ttcaactgct acgc 24

<210> SEQ ID NO 17
<211> LENGTH: 24
<212> TYPE: DNA
<213> ORGANISM: Primer for Fragment C

<400> SEQUENCE: 17
gcgtagcagt tgaactggcc ggtg 24

<210> SEQ ID NO 18
<211> LENGTH: 25
<212> TYPE: DNA
<213> ORGANISM: Primer for Fragment C

<400> SEQUENCE: 18
tttggaggag atccatgacg acata 25

<210> SEQ ID NO 19
<211> LENGTH: 25
<212> TYPE: DNA
<213> ORGANISM: Primer for Fragment C

<400> SEQUENCE: 19
tatgtcgtca tggatctcct ccaaa 25

<210> SEQ ID NO 20
<211> LENGTH: 25
<212> TYPE: DNA
<213> ORGANISM: Primer for Fragment C

<400> SEQUENCE: 20
tcttctcata tgctactgtg gggat 25

<210> SEQ ID NO 21
<211> LENGTH: 25
<212> TYPE: DNA
<213> ORGANISM: Primer for Fragment C

<400> SEQUENCE: 21
tgacatgcaa cacagggaca tgagc 25

<210> SEQ ID NO 22
<211> LENGTH: 25
<212> TYPE: DNA
<213> ORGANISM: Primer for Fragment D

<400> SEQUENCE: 22
catgctgacg aagagcgagg tcata 25

<210> SEQ ID NO 23
<211> LENGTH: 25
<212> TYPE: DNA
<213> ORGANISM: Primer for Fragment D

<400> SEQUENCE: 23
cccaggatat gaccttagtg gttgg 25

<210> SEQ ID NO 24
<211> LENGTH: 25
<212> TYPE: DNA

<213> ORGANISM: Primer for Fragment B

<400> SEQUENCE: 24
gaatggcaaa ctgggtccgc attac     25

<210> SEQ ID NO 25
<211> LENGTH: 25
<212> TYPE: DNA
<213> ORGANISM: Primer for Fragment B

<400> SEQUENCE: 25
gtaatgcgga cccagtttgc cattc     25

<210> SEQ ID NO 26
<211> LENGTH: 25
<212> TYPE: DNA
<213> ORGANISM: Primer for Fragment B

<400> SEQUENCE: 26
ctggttgttg tggcctggac gaaac     25

<210> SEQ ID NO 27
<211> LENGTH: 25
<212> TYPE: DNA
<213> ORGANISM: Primer for Fragment B

<400> SEQUENCE: 27
gtttcgtcca ggccacaaca accag     25

<210> SEQ ID NO 28
<211> LENGTH: 25
<212> TYPE: DNA
<213> ORGANISM: Primer for Fragment B

<400> SEQUENCE: 28
agcacaaacc ctacctatgt taggc     25

<210> SEQ ID NO 29
<211> LENGTH: 25
<212> TYPE: DNA
<213> ORGANISM: Primer for Fragment B

<400> SEQUENCE: 29
gcctaacata ggtagggttt gtgct     25

<210> SEQ ID NO 30
<211> LENGTH: 24
<212> TYPE: DNA
<213> ORGANISM: Primer for Fragment C

<400> SEQUENCE: 30
tggaatttcg cccggggcaa ggac     24

<210> SEQ ID NO 31
<211> LENGTH: 24
<212> TYPE: DNA
<213> ORGANISM: Primer for Fragment C

<400> SEQUENCE: 31
ccctgtgaca agtgctctgc tacg     24

<210> SEQ ID NO 32
<211> LENGTH: 24

```
<212> TYPE: DNA
<213> ORGANISM: Primer for Fragment C

<400> SEQUENCE: 32
tctgggatct cagtgcatcc aaca                                              24

<210> SEQ ID NO 33
<211> LENGTH: 26
<212> TYPE: DNA
<213> ORGANISM: Primer for Fragment C

<400> SEQUENCE: 33
gaagcatata tcagtcaaac ataacc                                            26

<210> SEQ ID NO 34
<211> LENGTH: 26
<212> TYPE: DNA
<213> ORGANISM: Primer for border between fragments A and B

<400> SEQUENCE: 34
cacatccttt gccttgctga atatgg                                            26

<210> SEQ ID NO 35
<211> LENGTH: 29
<212> TYPE: DNA
<213> ORGANISM: Primer for border between fragments A and B

<400> SEQUENCE: 35
cagtagtact aattaatcac cttagtagc                                         29

<210> SEQ ID NO 36
<211> LENGTH: 25
<212> TYPE: DNA
<213> ORGANISM: Primer for border between fragments B and C

<400> SEQUENCE: 36
cacgatcaac caaagaatgt cctcc                                             25

<210> SEQ ID NO 37
<211> LENGTH: 24
<212> TYPE: DNA
<213> ORGANISM: Primer for border between fragments B and C

<400> SEQUENCE: 37
tacttgtata tgcagctcca gcac                                              24
```